(12) United States Patent
O'Connor et al.

(10) Patent No.: US 11,773,365 B2
(45) Date of Patent: Oct. 3, 2023

(54) CELL CONCENTRATION METHODS AND DEVICES FOR USE IN AUTOMATED BIOREACTORS

(71) Applicant: LONZA WALKERSVILLE, INC., Walkersville, MD (US)

(72) Inventors: Joseph O'Connor, Walkersville, MD (US); Erika McAfee, Walkersville, MD (US); Samatha Bandapalle, Walkersville, MD (US); Yaling Shi, Walkersville, MD (US); Eytan Abraham, Walkersville, MD (US)

(73) Assignee: LONZA WALKERSVILLE, INC., Walkersville, MD (US)

( * ) Notice: Subject to any disclaimer, the term of this patent is extended or adjusted under 35 U.S.C. 154(b) by 0 days.

(21) Appl. No.: 16/782,181

(22) Filed: Feb. 5, 2020

(65) Prior Publication Data
US 2020/0255793 A1    Aug. 13, 2020

Related U.S. Application Data

(60) Provisional application No. 62/803,219, filed on Feb. 8, 2019.

(51) Int. Cl.
*C12M 1/00*     (2006.01)
*B01D 61/14*    (2006.01)
(Continued)

(52) U.S. Cl.
CPC .......... *C12M 47/02* (2013.01); *B01D 61/145* (2013.01); *B01D 71/34* (2013.01); *B01D 71/42* (2013.01);
(Continued)

(58) Field of Classification Search
CPC ...... C12M 29/00; C12M 33/14; C12M 41/48; C12M 41/30; C12M 23/42; C12M 29/04;
(Continued)

(56) References Cited

U.S. PATENT DOCUMENTS 4,642,120 A    2/1987   Nevo et al.
4,939,151 A    7/1990   Bacehowski et al.
(Continued)

FOREIGN PATENT DOCUMENTS

AU    2002/324169 A1    3/2003
DE        4021123 A1    4/1991
(Continued)

OTHER PUBLICATIONS

Cheng, et al.; Effects of gas slugs and inclination angle on the ultrafiltration flux in tubular membrane module Journal of Membrane Science vol. 158, Issues 1-2, Jun. 1, 1999, pp. 223-234 (Year: 1999).*

(Continued)

*Primary Examiner* — William H. Beisner
*Assistant Examiner* — Danielle B Henkel
(74) *Attorney, Agent, or Firm* — MEDLER FERRO WOODHOUSE & MILLS PLLC

(57) ABSTRACT

The present disclosure provides cassettes for use in automated cell engineering systems that include cell concentration filters for reducing fluid volume of a cell sample during or following automated processing. The disclosure also provides methods of concentrating a cell population, as well as automated cell engineering systems that can utilize the cassettes and carry out the methods.

12 Claims, 13 Drawing Sheets

(51) Int. Cl.
*C12M 1/36* (2006.01)
*B01L 3/00* (2006.01)
*C12M 1/34* (2006.01)
*B01D 71/52* (2006.01)
*B01D 71/34* (2006.01)
*B01D 71/42* (2006.01)

(52) U.S. Cl.
CPC .......... *B01D 71/52* (2013.01); *B01L 3/50273* (2013.01); *B01L 3/502715* (2013.01); *C12M 29/04* (2013.01); *C12M 41/26* (2013.01); *C12M 41/30* (2013.01); *C12M 41/48* (2013.01)

(58) Field of Classification Search
CPC ....... C12M 47/02; C12M 41/26; B01D 61/18; B01D 71/34; B01D 61/145; B01D 71/42; B01D 71/52; B01D 61/22; B01D 2315/10; B01D 2311/25; B01L 3/502715; B01L 3/50273
See application file for complete search history.

(56) References Cited

U.S. PATENT DOCUMENTS

| | | | |
|---|---|---|---|
| 5,041,138 A | 8/1991 | Vacanti et al. | |
| 5,081,036 A | 1/1992 | Familletti | |
| 5,240,854 A | 8/1993 | Berry et al. | |
| 5,246,699 A | 9/1993 | Debre et al. | |
| 5,424,209 A | 6/1995 | Kearney | |
| 5,478,479 A | 12/1995 | Herrig | |
| 5,549,134 A | 8/1996 | Browne et al. | |
| 5,688,687 A | 11/1997 | Palsson et al. | |
| 5,728,581 A | 3/1998 | Schwartz et al. | |
| 5,786,207 A | 7/1998 | Katz et al. | |
| 5,792,603 A | 8/1998 | Dunkelman et al. | |
| 5,827,729 A | 10/1998 | Naughton et al. | |
| 5,842,477 A | 12/1998 | Naughton et al. | |
| 5,846,828 A | 12/1998 | Peterson et al. | |
| 5,882,929 A | 3/1999 | Fofonoff et al. | |
| 5,891,455 A | 4/1999 | Sittinger et al. | |
| 5,902,741 A | 5/1999 | Purchio et al. | |
| 5,906,934 A | 5/1999 | Grande et al. | |
| 5,922,604 A | 7/1999 | Stapleton et al. | |
| 5,928,936 A | 7/1999 | Ingram | |
| 5,985,653 A | 11/1999 | Armstong et al. | |
| 5,989,913 A | 11/1999 | Anderson et al. | |
| 5,994,129 A | 11/1999 | Armstrong et al. | |
| 6,048,721 A | 4/2000 | Armstrong et al. | |
| 6,048,722 A | 4/2000 | Farb et al. | |
| 6,060,306 A | 5/2000 | Flatt et al. | |
| 6,096,532 A | 8/2000 | Armstrong et al. | |
| 6,121,042 A | 9/2000 | Peterson et al. | |
| 6,123,655 A | 9/2000 | Fell | |
| 6,197,575 B1 | 3/2001 | Griffith et al. | |
| 6,214,574 B1 | 4/2001 | Kopf | |
| 6,228,635 B1 | 5/2001 | Armstrong et al. | |
| 6,238,908 B1 | 5/2001 | Armstrong et al. | |
| 6,297,046 B1 | 10/2001 | Smith et al. | |
| 6,323,146 B1 | 11/2001 | Pugh et al. | |
| 6,402,941 B1 | 6/2002 | Lucido et al. | |
| 7,348,175 B2 | 5/2008 | Vilendrer et al. | |
| 7,906,323 B2 | 3/2011 | Cannon et al. | |
| 8,492,140 B2 | 7/2013 | Smith et al. | |
| 8,727,132 B2 | 5/2014 | Miltenyi et al. | |
| 9,499,780 B2 | 11/2016 | Smith et al. | |
| 9,534,195 B2 | 1/2017 | Smith et al. | |
| 9,629,877 B2 | 4/2017 | Cooper et al. | |
| 9,701,932 B2 | 7/2017 | Smith et al. | |
| 9,783,768 B2 | 10/2017 | Larcher et al. | |
| 10,131,876 B2 | 11/2018 | Kaiser et al. | |
| 10,253,316 B2 | 4/2019 | Masquelier et al. | |
| 10,273,300 B2 | 4/2019 | Bedoya et al. | |
| 11,208,626 B2 | 12/2021 | Mason et al. | |
| 2001/0021529 A1 | 9/2001 | Takagi | |
| 2001/0043918 A1 | 11/2001 | Masini et al. | |
| 2002/0009797 A1 | 1/2002 | Wolf et al. | |
| 2002/0009803 A1 | 1/2002 | Vajta | |
| 2002/0025547 A1 | 2/2002 | Rao | |
| 2002/0037580 A1 | 3/2002 | Schoeb | |
| 2002/0146816 A1 | 10/2002 | Vellinger et al. | |
| 2002/0155487 A1 | 10/2002 | Greenberger et al. | |
| 2002/0179525 A1 | 12/2002 | Shaffer et al. | |
| 2003/0032071 A1 | 2/2003 | Wang et al. | |
| 2003/0040104 A1 | 2/2003 | Barbera-Guillem | |
| 2003/0054335 A1 | 3/2003 | Taya et al. | |
| 2003/0159946 A1 | 8/2003 | Eden et al. | |
| 2003/0215935 A1 | 11/2003 | Coon | |
| 2004/0048364 A1 | 3/2004 | Trosch | |
| 2005/0064465 A1 | 3/2005 | Dettloff et al. | |
| 2005/0130297 A1 | 6/2005 | Sarem et al. | |
| 2005/0186671 A1 | 8/2005 | Cannon et al. | |
| 2011/0207209 A1 | 8/2011 | Hammons et al. | |
| 2013/0270165 A1* | 10/2013 | Shevitz | B01D 61/58 210/151 |
| 2014/0093952 A1 | 4/2014 | Serway | |
| 2015/0247114 A1 | 9/2015 | Gebauer | |
| 2015/0344844 A1 | 12/2015 | Better et al. | |
| 2016/0122782 A1 | 5/2016 | Crisman et al. | |
| 2017/0037369 A1 | 2/2017 | Ramsborg et al. | |
| 2017/0051252 A1 | 2/2017 | Morgan et al. | |
| 2019/0169572 A1 | 6/2019 | Shi et al. | |
| 2019/0211294 A1 | 7/2019 | Karnieli | |

FOREIGN PATENT DOCUMENTS

| | | |
|---|---|---|
| EP | 0248675 A1 | 12/1987 |
| GB | 1356794 A | 6/1974 |
| JP | 2-174848 A | 7/1990 |
| JP | 5-503418 A | 6/1993 |
| JP | 6-54678 A | 3/1994 |
| JP | 6-261736 A | 9/1994 |
| JP | H08-56646 A | 3/1996 |
| JP | H11-507229 A | 6/1999 |
| JP | 2001-275659 A | 10/2001 |
| KR | 20000023786 U | 9/2001 |
| WO | 91/05849 A1 | 5/1991 |
| WO | 93/03142 A1 | 2/1993 |
| WO | 1997/12960 A2 | 4/1997 |
| WO | 99/33951 A1 | 7/1999 |
| WO | 99/47922 A2 | 9/1999 |
| WO | 2000/046349 A1 | 8/2000 |
| WO | 01/02030 A2 | 1/2001 |
| WO | 2001/000783 A2 | 1/2001 |
| WO | 2002/028996 A1 | 4/2002 |
| WO | 02/088295 A1 | 11/2002 |
| WO | 03/022985 A2 | 3/2003 |
| WO | 03/087292 A2 | 10/2003 |
| WO | 2003/085101 A1 | 10/2003 |
| WO | 2015/162211 A1 | 10/2015 |
| WO | 2015175679 A2 | 11/2015 |
| WO | 2016/069993 A1 | 5/2016 |
| WO | 2016/118780 A1 | 7/2016 |
| WO | 2016/168275 A1 | 10/2016 |
| WO | 2017/068425 A1 | 4/2017 |
| WO | 2018/015561 A1 | 1/2018 |
| WO | 2018/136566 A1 | 7/2018 |

OTHER PUBLICATIONS

International Search Report and Written Opinion of the International Searching Authority from PCT/US20/16756, dated Jun. 15, 2020.

Andris et al., "Naïve T Cells are Resistant to Anergy Induction by Anti-CD3 Antibodies," The Journal of Immunology (2004) 173(5):3201-3208.

Atkuri et al., "Culturing at atmospheric oxygen levels impacts lymphocyte function," PNAS (2005) 102(10):3756-3759.

Austyn et al., "T cell activation by anti-CD3 antibodies: function of Fc receptors on B cell blasts, but not resting B cells, and CD18 on

(56) References Cited

OTHER PUBLICATIONS the responding T cells." European Journal of Immunology (1987) 17(9):1329-1335.

Avgoustiniatos et al., "Commercially Available Gas-Permeable Cell Culture Bags May Not Prevent Anoxia in Cultured or Shipped Islets," Transplant Proc. (2008) 40(2):395-400.

Baroja et al., "The anti-T cell monoclonal antibody 9.3 (Anti-CD28) provides a helper signal and bypasses the need for accessory cells in T Cell activation with immobilized anti-CD3 and mitogens," Cellular Immunology (1989) 120(1):205-217.

Berdeja et al., "First-in-human multicenter study of bb2121 anti-BCMA CAR T-cell therapy for relapsed/refractory multiple myeloma: Updated results," Journal of Clinical Oncology (2017) 35(15):3010.

Bohnenkamp et al., "Bioprocess development for the cultivation of human T-lymphocytes in a clincal scale," Cytotechnology (2002) 38:135-145.

Carpenter et al., "Non-Fc Receptor-Binding Humanized Anti-CD3 Antibodies Induce Apoptosis of Activated Human T Cells," The Journal of Immunology (2000) 165(11):6208-6213.

Ceuppens et al., "T cell unresponsiveness to the mitogenic activity of OKT3 antibody results from a deficiency of monocyte Fc gamma receptors for murine IgG2a inability to cross-link the T3-Ti complex," The Journal of Immunology (1985) 135(6):3882-3886.

Chai et al., "Immobilized anti-CD3 mAb induces anergy in murine naïve and memory CD4+ T cells in vitro.," Int Immunol. (1997) 9(7):935-944.

Charron et al., "Monocyte:T cell interaction regulates human T cell activation through a CD28/CD46 crosstalk," Immunol Cell Biol. (2015) 93(9):796-803.

Church et al., "Tumor-specific CD4+T cells maintain effector and memory tumor-specific CD8+T cells," European Journal of Immunology (2014) 44:69-79.

Clavreul et al., "Interelationship between CD3 and CD28 pathways in a murine T cell thymoma," Molecular Immunology (2000) 37(10):571-577.

Dudley et al., "Generation of Tumor-Infiltrating Lymphocyte Cultures for Use in Adoptive Transfer Therapy for Melanoma Patients," J Immunother. (2003) 26(4):332-342.

Fathman et al., "Molecular mechanisms of CD4+T-cell anergy," Nature Reviews Immunology (2007) 7:599-609.

FDA, Available online at: https://www.fda.gov/downloads/AdvisoryCommittees/CommitteesMeetingMaterials/Drugs/OncologicDrugsAdvisoryCommittee/UCM566166.pdf FDA, Regenerative Medicine Advanced Therapy Designation. (2017). Available at: https://www.fda.gov/BiologicsBloodVaccines/CellularGeneTherapyProducts/ucm537670.him. (Accessed: 8$^{th}$ Aug. 2017).

FDA, Sepax Cell Separation System and single use kits. (2011). Available at: https://www.fda.gov/downloads/BiologicsBloodVaccines/BloodBloodProducts/ApprovedProducts/SubstantiallyEquivalent510kDeviceinformation/UCM278385.pdf. (Accessed: 8$^{th}$ Nov. 2017).

Feldmann et al., "Novel humanized and highly efficient bispecific antibodies mediate killing of prostate stem cell antigen-expressing tumor cells by CD8+ and CD4+ T cells," J Immunol. (2012) 189(6):3249-3259.

Fleischer et al., "Differential expression and function of CD80 (B7-1) and CD86 (B7-2) on human peripheral blood monocytes," Immunology (1996) 89(4):592-598.

Gottschalk et al., The hype, hope and reality of personalization. The Medicine Maker (2015) p. 38-41.

Greenwald et al., "The B7 Family Revised," Annual Review of Immunology (2005) 23:515-548.

Grishagin, Ivan V., "Automatic cell counting with ImageJ," Analytical Biochemistry (2015) 473:63-65.

Hammill et al., "Designed ankyrin repeat proteins are effective targeting elements for chimeric antigen receptors," Journal for ImmunoTherapy of Cancer (2015) 3(55):1-11.

Harding et al., "CD28-mediated signalling co-stimulates murine T cells and prevents induction of anergy in T-cell clones," Nature (1992) 356:607-609.

Hasegawa et al., "In vitro Stimulation of CD8 and CD4 T Cells by Dendritic Cells Loaded with a Complex of Cholesterol-Bearing Hydrophobized Pullulan and NY-ESO-1 Protein: Identification of a New HLA-DR15-Binding CD4 T-Cell Epitope," Clinical Cancer Research (2006) 12(6):1921-1927.

Hollyman et al., "Manufacturing validation of biologically functional T cells targeted to CD19 antigen for autologous adoptive cell therapy," J Immunother. (2009) 32(2):169-180.

Ju et al., "A functional anti-human 4-1 BB ligand monoclonal antibody that enhances proliferation of monocytes by reverse signaling of 4-1 BBL," Hybrid Hybridomics (2003) 22(5):333-338.

Kaiser et al., "Towards a commercial process for the manufacture of genetically modified T cells for therapy," Cancer Gene Therapy (2015) 22:72-78.

Kalos et al., "T Cells with Chimeric Antigen Receptors Have Potent Antitumor Effects and Can Establish Memory in Patients with Advanced Leukemia," Sci Transl Med. (2011) 3(95):1-21.

Kebriaei et al., "Phase I trials using *Sleeping Beauty* to generate CD19-specific CAR T cells," The Journal of Clinical Investigation (2016) 126(9):3363-3376.

Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," Journal of Clinical Oncology (2016 33(6):540-549.

Lafferty et al., "A new analysis of allogeneic interactions," Aust J Exp Biol Med Sci. (1975) 53(1):27-42.

Laux et al., "Response Differences between Human CD4+ and CD8+ T-Cells during CD28 Costimulation: Implications for Immune Cell-Based Therapies and Studies Related to the Expansion of Double-Positive T-Cells during Aging," Clinical Immunology (2000) 96(3):187-197.

Ledbetter et al., "CD28 Ligation in T-cell Activation: Evidence for Two Signal Transduction Pathways," Blood (1990) 75(7):1531-1539.

Levine et al., "Global Manufacturing of CAR T Cell Therapy," Molecular: Therapy: Methods & Clinical Development (2017) 4:92-101.

Li et al., "Comparison of anti-CD3 and anti-CD28-coated beads with soluble anti-CD3 for expanding human T cells: Differing impact on CD8 T cell phenotype and responsiveness to restimulation," Journal of Translational Medicine (2010) 8(104):1-15.

Lock et al., "Automated Manufacturing of Potent CD20-Directed Chimeric Antigen Receptor T Cells for Clinical Use," Human Gene Therapy (2017) 28(10):914-925.

Locke et al., "Abstract CT019: Primary results from ZUMA-1: a pivotal trial axicabtagene ciloleucel (axicel; KTE-C19) in patients with refractory aggressive non-Hodgkin lymphoma (NHL)," Cancer Research (2017) 77(13).

Locke et al., "Phase 1 Results of ZUMA-1: A Multicenter Study of KTE-C19 Anti-CD19 CAR T Cell Therapy in Refractory Aggressive Lymphoma," Molecular Therapy (2017) 25(1):285-295.

Lu et al., "A Rapid Cell Expansion Process for Production of Engineered Autologous CAR-T Cell Therapies," Human Gene Therapy Methods (2016) 27(6):209-218.

Lu et al., "Automated dynamic fed-batch process and media optimization for high productivity cell culture process development," Biotechnology and Bioengineering (2013) 110(1):191-205.

Lu et al., "Treatment of Patients with Metastatic Cancer Using a Major Histocompatibility Complex Class II-Restricted T-Cell Receptor Targeting the Cancer Germline Antigen MAGE-A3," Journal of Clinical Oncology (2017) 35(29):3322-3329.

Mock et al., "Automated manufacturing of chimeric antigen receptor T cells for adoptive immunotherapy using CliniMACS Prodigy," Cytotherapy (2016) 18(8):1002-1011.

Morrissey et al., "End-to-End Cell Therapy Automation: An Immunotherapy Case Study," BioPharm International (2017) 2:10-18.

Nilsson et al., "Optimal Blood Mononuclear Cell Isolation Procedures for Gamma Interferon Enzyme-Linked Immunospot Testing

(56) References Cited

OTHER PUBLICATIONS of Healthy Swedish and Tanzanian Subjects," Clinical and Vaccine Immunology (2008) 15(4):585-589.
Nociari et al., "A novel one-step, highly sensitive fluorometric assay to evaluate cell-mediated cytotoxicity," Journal of Immunological Methods (1998) 213(2):157-167.
Odeleye et al., "On the fluid dynamics of a laboratory scale single-use stirred bioreactor," Chemical Engineering Science (2014) 111(100):299-312.
Reusch et al., "A tetravalent bispecific TandAb (CD19/CD3), AFM11, efficiently recruits T cells for the potent lysis of CD19+ tumor cells," MAbs (2015) 7(3):584-604.
Riddell et al., "Adoptive Therapy with Chimeric Antigen Receptor Modified T Cells of Defined Subset Composition," Cancer J (2014) 20(2):141-144.
Riddell et al., "The use of anti-CD3 and anti-CD28 monoclonal antibodies to clone and expand human antigen-specific T cells," Journal of Immunological Methods (1990) 128(2):189-201.
Romagnani, S, "Type 1 T helper and type 2 T helper cells: functions, regulation and role in protection and disease," Int J Clin Lab Res (1991) 21(2):152-158.
Schwartz, RH, "A cell culture model for T lymphocyte clonal anergy," Science (1990) 248(4961): 1349-1356.
Schwartz, RH, "T cell anergy," Annu Rev Immunol. (2003) 21:305-334.
Tangying et al., "A Rapid Cell Expansion Process for Production of Engineering Autologous CAR-T Cell Therapies," Human Gene Therapy Methods (2016) 27(6):209-218.
Tax et al., "Polymorphism in mitogenic effect of IgG1 monoclonal antibodies against T3 antigen on human T cells," Nature (1983) 304(5925):445:447.
Trainor et al., "Rethinking clinical delivery of adult stem cell therapies," Nature Biotechnology (2014) 32:729-735.
Trickett et al., "T cell stimulation and expansion using anti-CD3/CD28 beads," Journal of Immunological Methods (2003) 275(1-2):251-255.
Tuefferd et al., "HER2 Status in Ovarian Carcinomas: A Multicenter GINECO Study of 320 Patients," PLoS ONE (2007) 11:e1138.
Turtle et al., "CD19 CAR-T cells of defined CD4+ :CD8+ composition in adult B cell ALL patients," The Journal of Clinical Investigation (2016) 126(6):2123-2138.
Vanseggelen et al., "Chimeric antigen receptor—engineered T cells as oncolytic virus carriers," Molecular Therapy—Oncolytics (2015) 150014.
Verwilghen et al., "Differences in the stimulating capacity of immobilized anti-CD3 monoclonal antibodies: variable dependence on interleukin-1 as a helper signal for T-cell activation," Immunology (1991) 72:269-276.
Wang et al., "Clinical manufacturing of CAR T cells: foundation of a promising therapy" Mol. Ther.—Oncolytics (2016) 3:16015.
Wang et al., "Manufacture of tumor—and virus-specific T lymphocytes for adoptive cell therapies," Cancer Gene Ther. (2015) 22(2):85-94.
Wauwe et al., "OKT3: a monoclonal anti-human T lymphocyte antibody with potent mitogenic properties," The Journal of Immunology (1980) 124(6):2708-2713.
Wegener, C, "Cell Washing with the LOVO Cell Processing System," BioProcess International (2014) p. 78.
Weiss et al., "T cell activation: differences in the signals required for IL 2 production by nonactivated and activated T cells," J Immunol (1985) 135(6):3669-3673.
Wolf et al., "Induction of anergy in resting human T lymphocytes by immobilized anti-CD3 antibodies," European Journal of Immunology (1994) 24(6):1410-1417.
Yan et al., "HER2 expression status in diverse cancers: review of results from 37,992 patients," Cancer Metastasis Rev (2015) 34:157-164.
Zhu et al., "CD137 stimulation delivers an antigen-independent growth signal for T lymphocytes with memory phenotype," Immunobiology (2007) 109(11):4882-4889.

Konstantin B. Konstantinov "Monitoring and Control of the Physiological State of Cell Cultures" Biotechnology and Bioengineering, vol. 52, pp. 271-289 (1996) (Year: 1996).
Farndale "Pulsed Electromagnetic Fields Promote Collagen Production in Bone Marrow Fibroblasts via Athermal Mechanisms" Calcif Tissue Int (1985) 37:178-182.
Aitken-Christie et al., Automation in Plant tissue culture—general introduction and overview, in Automation and Environmental Control in Plant Tissue Culture 757 (J. Aitken-Christie, T. Kozai & M. Lila Smith eds., 1995).
Apel et al., Integrated Clinical Scale Manufacturing System for Cellular Products Derived by Magnetic Cell Separation, Centrifugation and Cell Culture, Chemie Ingenieur Technik (2013).
Armstrong et al., Clinical Systems for the Production of Cells and Tissues for Human Therapy, in Novel Therapeutics From Modern Biotechnology 221 (D.L. Oxender et al. eds., 1999).
Blaeschke et al., Induction of A Central Memory and Stem Cell Memory Phenotype in Functionally Active CD4+ and CD8+ CAR T Cells Produced in an Automated Good Manufacturing Practice System for the Treatment of CD19+ Acute Lymphoblastic Leukemia, Cancer Immunology, Immunotherapy vol. 67, pp. 1053-1066 (2018), published Mar. 31, 2018.
Bousso, T-cell activation by dendritic cells in the lymph node: lessons from the movies, 8 Nature Reviews Immunology 675 (2008) ("Bousso 2008").
Declaration from Mark Selker, Submitted in *Lonza Walkersville, Inc. v. Adva Biotechnology LTD.*, United States District Court for the District of Maryland, Case No. 8:20-cv-03099-PX, Jan. 5, 2022.
Declaration from James C. Leung, Submitted in *Lonza Walkersville, Inc. v. Adva Biotechnology LTD.*, United States District Court for the District of Maryland, Case No. 8:20-cv-03099-PX, Jan. 7, 2022.
Kempner et al., A Review of Cell Culture Automation, 7 Journal of the Association for Laboratory Automation 56 (2002) ("Kempner 2002").
Koller et al., Clinical-scale human umbilical cord blood cell expansion in a novel automated perfusion culture system, Bone Marrow Transplantation (1998) ("Koller 1998").
Koller et al., Large-Scale Expansion of Human Stem and Progenitor Cells from Bone Marrow Mononuclear Cells in Continuous Perfusion Cultures, BLOOD (1993) ("Koller 1993A").
Koller et al., Tissue Engineering: Reconstitution of Human Hematopoiesis Ex Vivo, Biotechnology and Bioengineering (1993) ("Koller 1993B").
Kostov et al., Low-Cost Microbioreactor for High-Throughput Bioprocessing, 72 Biotechnology and Bioengineering, Feb. 5, 2001 ("Kostov 2001").
Krug et al., A GMP-compliant protocol to expand and transfect cancer patient T cells with mRNA encoding a tumor-specific chimeric antigen receptor, Cancer Immunol Immunotherapy (2014) ("Krug 2014").
Morse, Technology evaluation: Stem-cell therapy, Aastrom Biosciences Inc., Current Opinion in Molecule Therapeutics (1999) ("Morse 1999").
Oh et al., Frequent Harvesting from Perfused Bone Marrow Cultures Results in Increased Overall Cell and Progenitor Expansion, Biotechnology and Bioengineering (1994).
Priesner et al., Automated Enrichment, Transduction, and Expansion of Clinical—Scale CD62L+ T Cells for Manufacturing of Gene Therapy Medicinal Products, 27 Human Gene Therapy 10, 860-869 (2016).
Rosazza et al., Gene Electrotransfer: A Mechanistic Perspective, Current Gene Therapy (2016) ("Rosazza 2016").
Shi et al., "Performance of Mammalian Cell Culture Bioreactor with a New Impeller Design" Biotechnology and Bioengineering, vol. 40, pp. 260-270 (1992).
Stiff et al., Autologous transplantation of ex vivo expanded bone marrow cells grown from small aliquots after high-dose chemotherapy for breast cancer, BLOOD (2000) ("Stiff 2000").
Wang et al., Manufacture of Tumor—and Virus-specific T Lymphocytes for Adoptive Cell Therapies, 22 Cancer Gene Therapy 2 (2015).

(56) References Cited

OTHER PUBLICATIONS

Zhang et al., Characterization of clinical grade CD19 chimeric antigen receptor T cells produced using automated CliniMACS Prodigy system, Drug Design, Development and Therapy (2018) ("Zhang 2018").
Zhu et al., Closed-system manufacturing of CD19 and dual-targeted CD20/19 chimeric antigen receptor T cells using the CliniMACS Prodigy device at an academic medical center, CYTOTHERAPY (2018).
Singapore Search Report for SG 11202108473X dated May 9, 2023.

* cited by examiner

US 11,773,365 B2

CELL CONCENTRATION METHODS AND DEVICES FOR USE IN AUTOMATED BIOREACTORS

CROSS-REFERENCE TO RELATED APPLICATIONS

The present application claims benefit of U.S. Provisional Patent Application No. 62/803,219, filed Feb. 8, 2019, the disclosure of which is incorporated by reference herein in its entirety.

FIELD OF THE INVENTION

The present disclosure provides cassettes for use in automated cell engineering systems that include cell concentration filters for reducing fluid volume of a cell sample during or following automated processing. The disclosure also provides methods of concentrating a cell population, as well as automated cell engineering systems that can utilize the cassettes and carry out the methods.

BACKGROUND OF THE INVENTION

As anticipation builds about accelerated clinical adoption of advanced cell therapies, more attention is turning to the underlying manufacturing strategies that will allow these therapies to benefit patients worldwide. While cell therapies hold great promise clinically, high manufacturing costs relative to reimbursement present a formidable roadblock to commercialization. Thus, the need for cost effectiveness, process efficiency and product consistency is driving efforts for automation in numerous cell therapy fields.

Automation of various processes is involved in producing cell populations for therapy. This includes integration of cell activation, transduction and expansion into a commercial manufacturing platform, for the translation of these important therapies to the broad patient population.

It is often necessary to reduce the volume of a cell population, either during automated processing, or prior to a final output from the automated system. What is needed is a process by which a cellular sample can be concentrated, i.e., the volume of the sample reduced, either during the automation or prior to a sample output.

SUMMARY OF THE INVENTION

In some embodiments, provided here is a cassette for use in an automated cell engineering system, comprising a cell culture chamber, a pumping system fluidly connected to the cell culture chamber, a tangential flow filter fluidly connected to the pumping system, wherein the pumping system provides a retentate flow to the tangential flow filter and wherein a permeate flow of the tangential flow filter is controlled by a flow controller, and a cellular sample output fluidly connected to the tangential flow filter.

In further embodiments, provided herein is a cassette for use in an automated cell engineering system, comprising a cell culture chamber, a pumping system fluidly connected to the cell culture chamber, a tangential flow filter fluidly connected to the pumping system, wherein the pumping system provides a retentate flow to the tangential flow filter and wherein a permeate flow of the tangential flow filter is controlled by a flow controller, a satellite volume connected to the tangential flow filter, a fluidics pathway for recirculating the retentate flow back through the tangential flow filter, a fixed volume waste collection chamber fluidly connected to the tangential flow filter, and a cellular sample output fluidly connected to the tangential flow filter.

In additional embodiments, provided herein is a method of reducing a volume of a cellular sample during automated processing, the method comprising introducing a cellular sample into a tangential flow filter having a retentate flow and a permeate flow, wherein the permeate flow is controlled by a flow controller, passing the cellular sample through the retentate flow of the tangential flow filter, removing volume from the cellular sample via the permeate flow to a fixed volume waste collection chamber, and collecting the cellular sample having the reduced volume.

In still further embodiments, provided herein is an automated cell engineering system, comprising an enclosable housing, a cassette contained within the enclosable housing, the cassette comprising a cell culture chamber, a pumping system fluidly connected to the cell culture chamber, a tangential flow filter fluidly connected to the pumping system, wherein the pumping system provides a retentate flow to the tangential flow filter and wherein a permeate flow of the tangential flow filter is controlled by a flow controller, and a cellular sample output fluidly connected to the tangential flow filter, and a user interface for receiving input from a user.

DETAILED DESCRIPTION OF THE INVENTION

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined. Reference is made herein to various methodologies and materials known to those of skill in the art.

Figure 1:
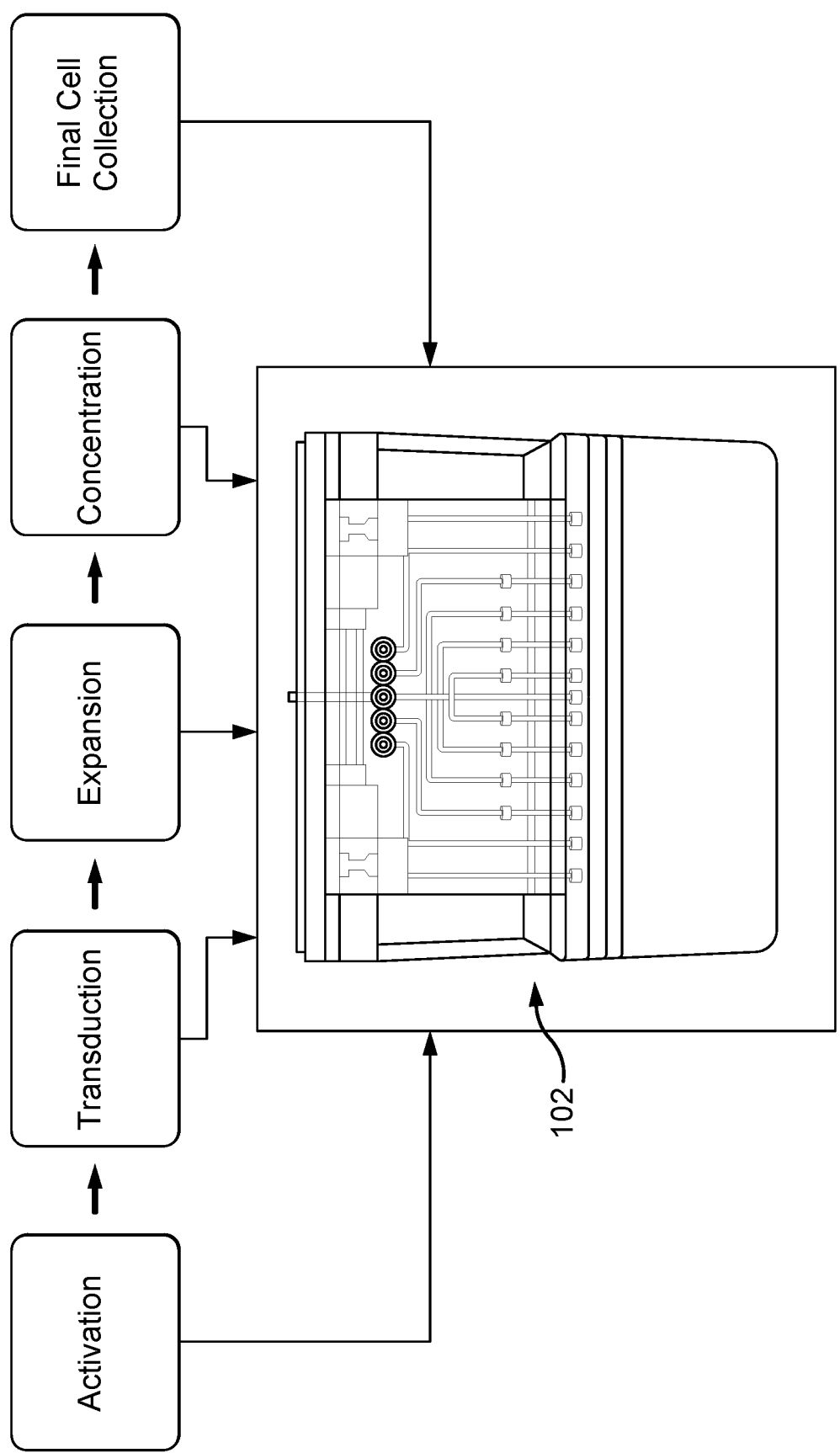
FIG. 1 shows various steps that can be performed with a cassette of an automated cell engineering system, as described in embodiments hereof.

In embodiments, provided herein are cassettes for use in an automated cell engineering system. FIG. 1 shows an exemplary cassette 102, in which various processes can be carried out in an enclosed, automated system that allows for production of various cellular samples and populations. Such processes can include activating, transducing, expanding, concentrating, washing, and collecting/harvesting steps.

As described herein, the cassettes and methods are utilized and carried out in a fully enclosed automated cell engineering system 300 (see FIGS. 3A, 3B), suitably having instructions thereon for performing steps such as, activating, transducing, expanding, concentrating, and harvesting. Cell engineering systems for automated production of, for example genetically modified immune cells, including CAR T cells, are described in U.S. patent application Ser. No. 16/119,618, filed Aug. 31, 2018 (the disclosure of which is incorporated by reference herein in its entirety), and are also called automated cell engineering system, COCOON™, or COCOON™ system herein.

For example, a user can provide an automated cell engineering system pre-filled with a cell culture and reagents (e.g., an activation reagent, a vector, cell culture media, nutrients, selection reagent, and the like) and parameters for the cell production (e.g., starting number of cells, type of media, type of activation reagent, type of vector, number of cells or doses to be produced, and the like). The automated cell engineering system is able to carry out the various automated methods, including methods of producing genetically modified immune cell cultures, including CAR T cells, without further input from the user. In some embodiments, the fully enclosed automated cell engineering system minimizes contamination of the cell cultures by reducing exposure of the cell culture to non-sterile environments. In additional embodiments, the fully enclosed automated cell engineering system minimizes contamination of the cell cultures by reducing user handling of the cells.

As described herein, the automated cell engineering systems 300 suitably include a cassette 102. Thus, in embodiments, provided herein is a cassette for use in an automated cell engineering system. As used herein a "cassette" refers to a largely self-contained, removable and replaceable element of a automated cell engineering system that includes one or more chambers for carrying out the various elements of the methods described herein, and suitably also includes one or more of a cell media, an activation reagent, a wash media, etc.

Figure 2A:
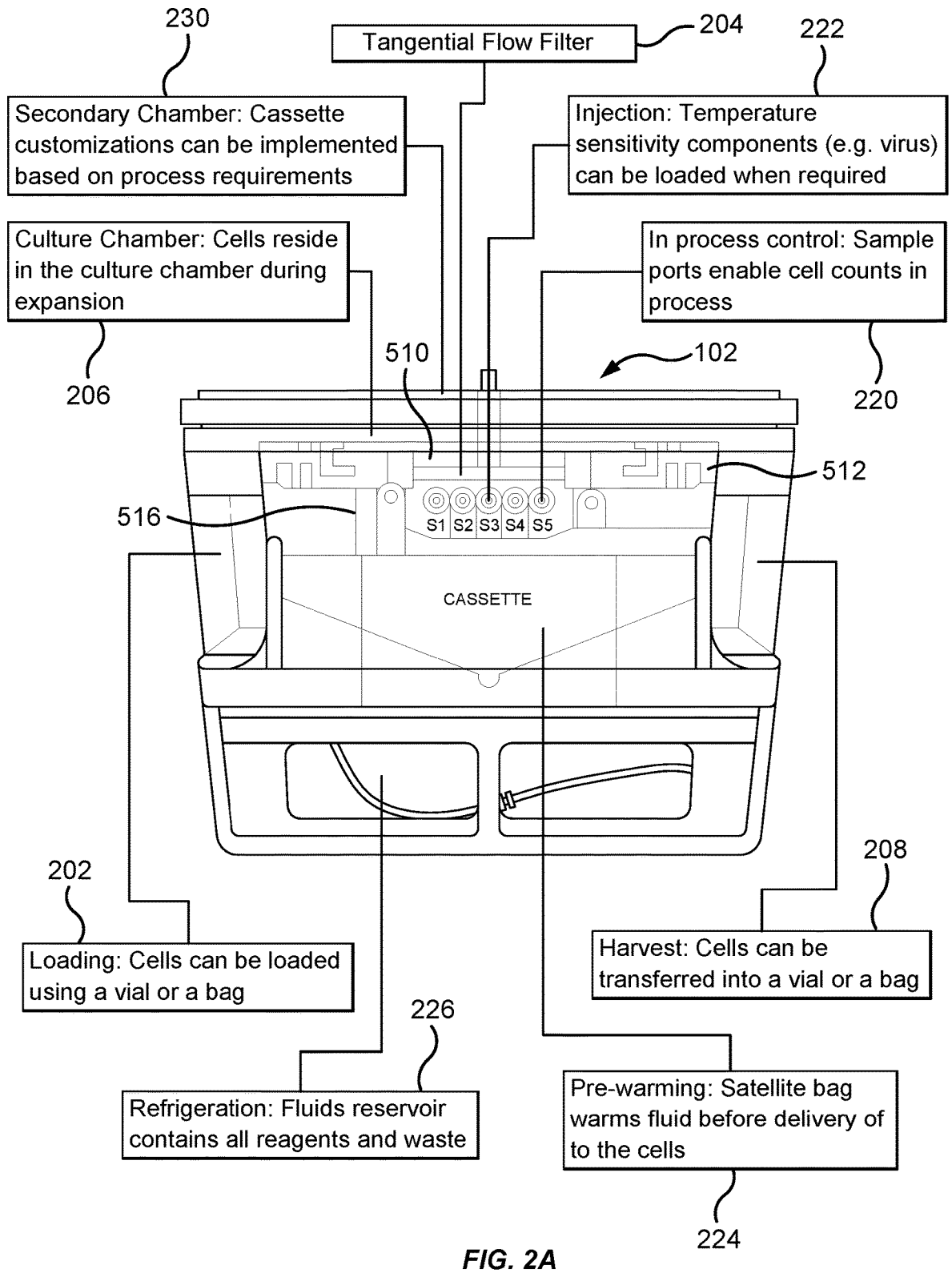
FIG. 2A shows an exemplary cassette in accordance with embodiments hereof.

FIG. 2A shows an exemplary cassette 102 for use in an automated cell engineering system. In embodiments, cassette 102 includes a cellular sample input 202. Cellular sample input 202 is shown in FIG. 2A as a vial or chamber in which a cellular sample can be placed prior to introduction or loading into cassette 102. In other embodiments, cellular sample input 202 can simply be a sterile-locking tubing (for example a luer lock tubing connection or the like) to which a syringe or a cell-containing bag, such as a blood bag, can be connected.

Cassette 102 further includes a cell culture chamber 206. Examples of the characteristics and uses of cell culture chamber 206 are described herein. Cassette 102 also includes a pumping system 520 (see FIG. 5 for exemplary location in the flowpath) fluidly connected to cell culture chamber 206.

As used herein, "fluidly connected" means that one or more components of a system, such as components of cassette 102, are connected via a suitable element that allows for fluids (including gasses and liquids) to pass between the components without leaking or losing volume. Exemplary fluid connections include various tubing, channels and connections known in the art, such as silicone or rubber tubing, luer lock connections, etc. It should be understood that components that are fluidly connected can also include additional elements between each of the components, while still maintaining a fluid connection. That is, fluidly connected components can include additional elements, such that a fluid passing between the components can also pass through these additional elements, but is not required to do so.

Pumping system 520 is suitably a peristaltic pump system, though other pumping systems can also be utilized. A peristaltic pump refers to a type of positive displacement pump for pumping a fluid. The fluid is suitably contained within a flexible tube fitted inside a pump casing—often circular. A rotor with a number of "rollers", "shoes", "wipers", or "lobes" attached to the external circumference of the rotor compresses the flexible tube. As the rotor turns, the part of the tube under compression is pinched closed (or "occludes") thus forcing the fluid to be pumped to move through the tube. Additionally, as the tube opens after the passing of the cam ("restitution" or "resilience") fluid flow is induced to the pump. This process is called peristalsis and is used to move fluid through the flexible tube. Typically, there are two or more rollers, or wipers, occluding the tube, trapping between them a body of fluid. The body of fluid is then transported toward the pump outlet.

Figure 2B:
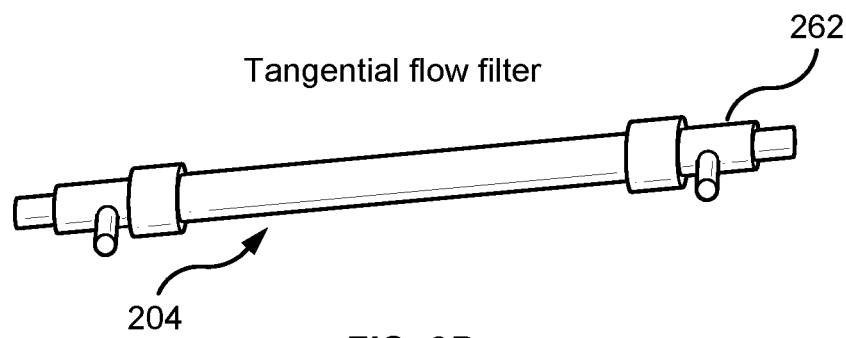
FIG. 2B shows an exemplary tangential flow filter for use in the cassettes, systems and methods described herein.
Figure 2C:
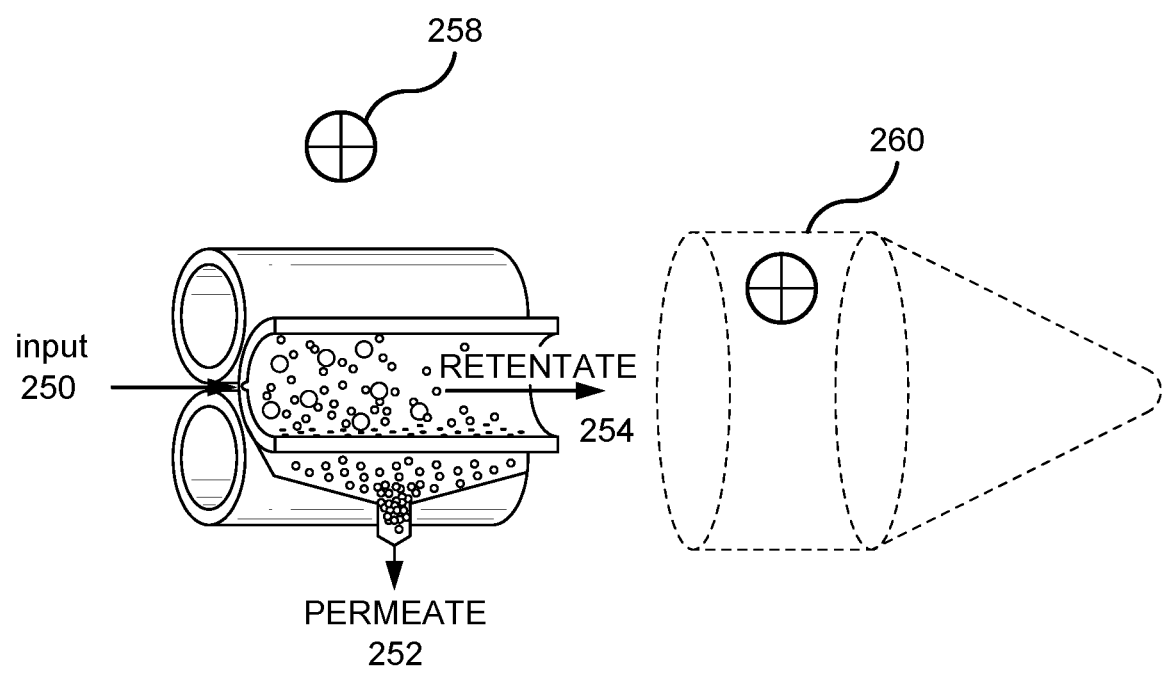
FIG. 2C shows exemplary flow controllers for use with the tangential flow filters as described herein.

Cassette 102 also includes a tangential flow filter 204 fluidly connected to the pumping system. FIG. 2B shows an exemplary tangential flow filter. FIG. 2C shows a schematic of an interior of a tangential flow filter. Tangential flow filtration, also known as crossflow filtration, is a filtration system or process where a feed, inlet or input fluid stream (250 in FIG. 2C) passes parallel to a membrane face as one portion passes through, and out of the membrane (permeate flow—252 in FIG. 2C) while the remainder (retentate flow—254 in FIG. 2C) passes within the membrane and can be recirculated back to the input, becomes concentrated, can ultimately be passed to a storage or output.

Tangential flow filter 204 is suitably comprised of a series of hollow fiber membranes (though a single fiber can also be used), into which a solution is fed. The retentate flow passes within the hollow fiber, retaining cells within the solution inside of the fiber membrane, while excess volume passes through the fiber membrane and out into the permeate flow. This reduces the volume of the total cellular sample, resulting in a concentration of the cellular sample. The membranes are suitably provided in the form of a self-contained apparatus, which can include a flow controller 258.

As described herein, with reference to FIG. 2C, pumping system 520 provides retentate flow 254 to tangential flow filter 204, while permeate flow 252 of the tangential flow filter is controlled by a flow controller 258. "Flow controller" as used herein refers to a valve, constriction device, flow diverter, pump mechanism, fluidics—including various tubing set-ups, or other mechanisms, to control the amount of fluid that leaves the fiber membrane of the tangential flow filter and enters the permeate flow. Flow controller 258 in FIG. 2C is provided simply to illustrate the inclusion of a mechanism for controlling the amount of permeate flow 252, and is does not indicate the structure of this mechanism.

In exemplary embodiments, flow controller 258 is a flow restrictor 260. "Flow restrictor" refers to a valve, gradually narrowing tubing, or constriction device, to control the amount and rate of permeate flow 252 exiting the tangential flow filter. Flow restriction 260 is placed downstream of tangential flow filter 204, so that the control of permeate flow occurs after exciting the membranes of tangential flow filter 204. Flow restrictor 260 is shown in FIG. 2C for illustrative purposes only, and the location and workings of flow restrictor 260 are not to be limited by the representation in FIG. 2C. A person of ordinary skill the art will readily appreciate the various ways that the flow restrictor can be used to control the amount and rate of permeate flow 252. Suitably, flow restrictor 260 is placed adjacent an end 262 of tangential flow filter 204 (see FIG. 2B), to restrict the amount and rate of permeate flow 252.

In further embodiments, flow controller 258 is an additional pumping system 521 that can be set up to control and restrict (or increase) the amount and rate of permeate flow 252.

In still further embodiments, flow controller 258 is a system having a plurality of tubing that can also be orientated and placed within cassette 102 to provide desired control (restriction or increase) of the amount and rate of permeate flow 252.

In embodiments, cassette 102 further includes one or more fluidics pathways suitably connected to the cell culture chamber (see inside cassette 102 in FIG. 2A). Also included in cassette 102 is a cellular sample output 208 fluidly connected to cell culture chamber. The cassette 102 also suitably includes a cellular sample output 208 fluidly connected to tangential flow filter 204.

As described herein, cellular sample output 208 can be utilized to harvest the cells following the various automated procedures for either further processing, storage, or potential use in a patient. Cellular sample output 208 can also be a sample port 220, as described herein, that allows a cellular sample to be removed from the cassette, for example for transduction such as electroporation, and then returned to the cassette for further automated processing. Examples of fluidics pathways include various tubing, channels, capillaries, microfluidics elements, etc., that provide nutrients, solutions, etc., to the elements of the cassette, as described herein. Cellular sample output 208 can also simply be the output of the tangential flow filter, which is then fluidly connected to another section or portion of cassette 102 as described herein.

In embodiments, cassette 102 explicitly excludes a centrifuge before or following tangential flow filter 204. It has been determined that through the use of the various cell separation filters and methods described herein, additional cellular separation via centrifugation procedures and the use of a centrifuge is not required. In embodiments, however, an additional filtration system, such as a column filtration, and/or magnetic filtration system, can be utilized.

In exemplary embodiments, tangential flow filter 204 includes a membrane which has a pore size of about 0.40 µm to about 0.80 µm and a fiber diameter of about 0.5 mm to about 0.9 mm. In embodiments, the pore size of tangential flow filter 204 is about 0.2 µm to about 1.0 µm, or about 0.3 µm to about 0.9 µm, about 0.4 µm to about 0.8 µm, about 0.5 µm to about 0.7 µm, about 0.6 µm to about 0.7 µm, or about 0.40 µm, about 0.45 µm, about 0.50 µm, about 0.55 µm, about 0.60 µm, about 0.65 µm, about 0.70 µm, about 0.75 µm, or about 0.80 µm. In embodiments, the fiber diameter is about 0.30 mm to about 1.2 mm, suitably about 0.40 mm to about 1.0 mm, about 0.50 mm to about 0.90 mm, about 0.60 mm to about 0.80 mm, about 0.70 mm to about 0.80 mm, or about 0.60 mm, about 0.65 mm, about 0.70 mm, about 0.75 mm, about 0.80 mm, about 0.85 mm, or about 0.90 mm.

Suitably, tangential flow filter 204 comprises about 15-20 fibers, suitably 18 filters, having a total length of the lumen of the fibers of between about 10-20 cm, suitably about 10-15 cm, or about 13 cm. The surface area of the fibers is on the order of about 40-70 $cm^2$, more suitably about 50-60 $cm^2$, or about 57 $cm^2$. In embodiments, a relatively high surface area, large pore size membrane is desired for use in tangential flow filter 204.

Exemplary materials for use in tangential flow filter 204 include polymers, including but not limited to, poly(ether sulfone), poly(acrylonitrile) and poly(vinylidene difluoride), cellulose esters, poly(sulfone). Exemplary tangential flow filters include those available from SPECTRUM LABS®, including MICROKROS® and MIDIKROS® filters, and modifications thereof to fit inside a desired cassette. In embodiments, the material is a modified poly(ether sulfone).

In further embodiments, a coating can be applied to the surface of the tangential flow filter. Suitably, this coating can help to reduce or eliminate fouling on the surface of tangential flow filter 204. Exemplary non-fouling coatings include, for example, phospholipid coatings, polymeric coatings, such as poly(vinyl alcohol) (PVA), poly(ethylene glycol) coatings, etc. Additional surface coatings can also be applied to the tangential flow filter to provide stability, increased or decreased flow, or other desired characteristics.

In further embodiments, additional pre- and post-filters (i.e., before or after the tangential flow filter) can also be utilized in the cassettes and methods described herein. For example, a magnetic separation process can be utilized to further eliminate and separate undesired cells and debris from a cell population. In such embodiments, a magnetic bead or other structure, to which a biomolecule (e.g., antibody, antibody fragment, etc.) has been bound, can interact with a target cell. Various magnetic separation methods, including the use of filters, columns, flow tubes or channels with magnetic fields, etc., can then be used to separate the target cell population from undesired cells, debris, etc., that may be in a cellular sample. For example, a target cell population can flow through a tube or other structure and be exposed to a magnetic field, whereby the target cell population is retained or held-up by the magnetic field, allowing undesired cells and debris to pass through the tube. The magnetic field can then be turned off, allowing the target cell population to pass onto a further retention chamber or other area(s) of the cassette for further automated processing. Additional filtration includes traditional column filtration, or use of other filtration membranes and structures.

In further embodiments, cassette 102 further includes a fixed volume waste collection chamber 510 fluidly connected to tangential flow filter 204. Fixed volume waste collection chamber 510 is used to collect permeate flow 252 exiting the tangential flow filter. By utilizing a fixed volume, the fixed volume waste collection chamber is allowed to only hold a pre-determined about of collected permeate flow 252. Once this pre-determined amount of permeate flow 252 is reached, no additional permeate flow 252 is allowed to exit tangential flow filter 204, and thus the volume of the cellular sample will not be further reduced. This results in a cell concentration and cellular sample volume having a pre-defined and known value, for example, pre-defined to meet an end goal or for further processing of a defined volume. Examples of fixed volume waste collection chambers 510 include various hard plastics, metals, etc., that will not expand and thus only hold a fixed volume. In addition, a bag or flexible plastic can be used, but can be placed inside of a hard plastic vessel or between non-moving walls (e.g., plastic walls), such that once the bag reaches a pre-determined volume, it impinges upon the non-moving walls or vessel, and the expansion of the bag stops. As the fixed volume waste collection chamber 510 fills to capacity, no additional permeate flow 252 is allowed to exit, and the retentate flow 254 then simply recirculates through the tangential flow filter, until such time as collection is desired. Suitably, this recirculation occurs via a fluidics pathway (i.e., shown generically as 540 in the flowpath of FIG. 5. Fixed volume waste collection chamber 510 can also include a level monitor that will trigger and direct the permeate flow 252 to stop and recirculate the retentate flow 254.

Figure 5:
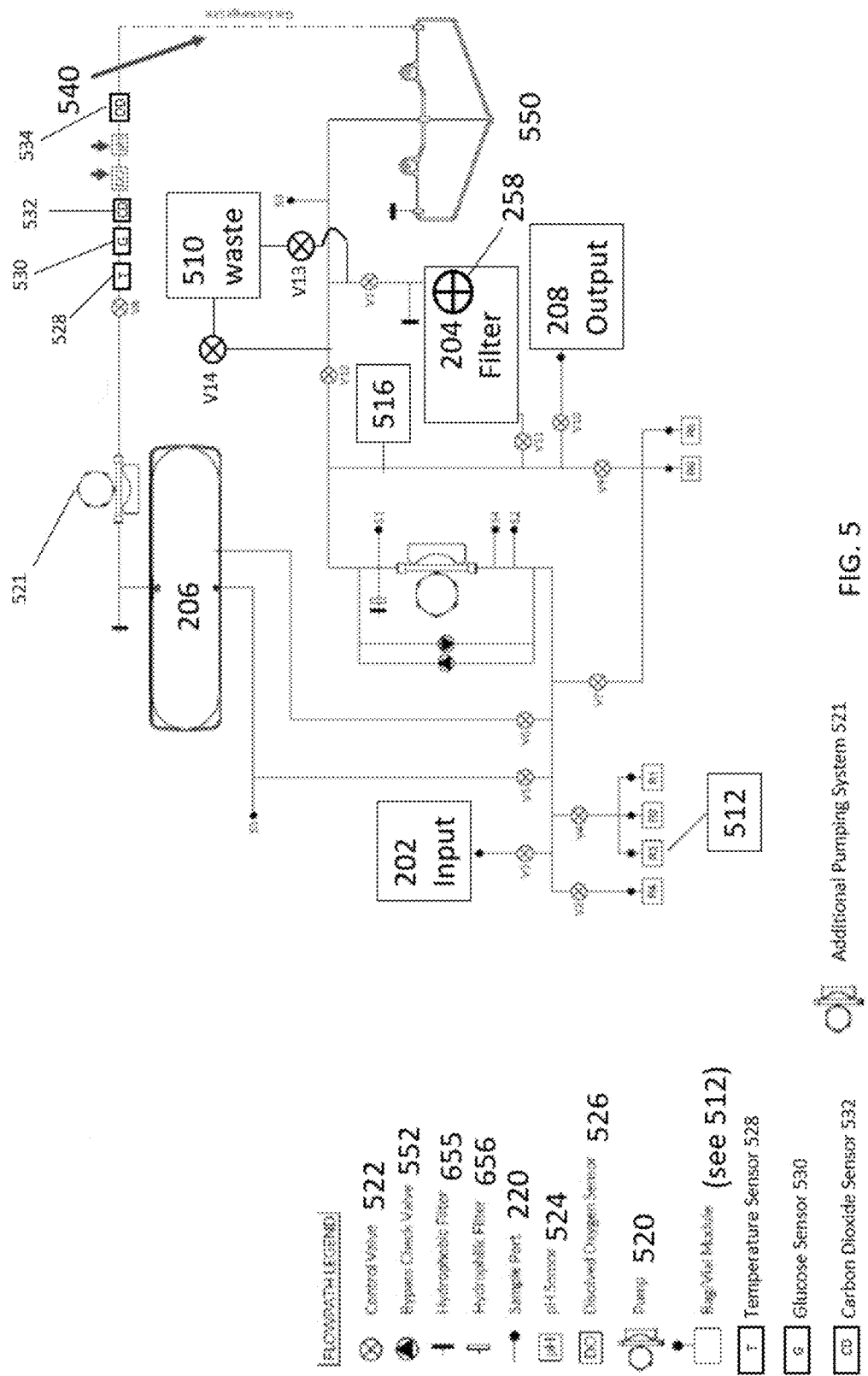
FIG. 5 shows a flowpath for cell concentration in a cassette of an automated cell engineering system as described in embodiments hereof.

In additional embodiments, a satellite volume 550, which can be provide additional storage capabilities for the cassette, to increase the overall volume of the automated processes, or additional volume flow for the tangential flow filtration, is fluidly connected to tangential flow filter 204. An exemplary location of satellite volume 550 is shown in the flowpath of FIG. 5.

The cassettes can also further include one or more fluidics pathways (generically 540), wherein the fluidics pathways provide recirculation, removal of waste and homogenous gas exchange and distribution of nutrients to various parts of the cassette, including the cell culture chamber without disturbing cells within the cell culture chamber. Cassette 102 also further includes one or more valves 522 or 552, for controlling the flow through the various fluidic pathways (see FIG. 5 for exemplary locations within flowpath).

In exemplary embodiments, as shown in FIG. 2A, cell culture chamber 206 is a flat and non-flexible chamber (i.e., made of a substantially non-flexible material such as a plastic) that does not readily bend or flex. The use of a non-flexible chamber allows the cells to be maintained in a substantially undisturbed state. As shown in FIG. 2A, cell culture chamber 206 is oriented so as to allow the immune cell culture to spread across the bottom of the cell culture chamber. As shown in FIG. 2A, cell culture chamber 206 is suitably maintained in a position that is parallel with the floor or table, maintaining the cell culture in an undisturbed state, allowing the cell culture to spread across a large area of the bottom of the cell culture chamber. In embodiments, the overall thickness of cell culture chamber 206 (i.e., the chamber height) is low, on the order of about 0.5 cm to about 5 cm. Suitably, the cell culture chamber has a volume of between about 0.50 ml and about 300 ml, more suitably between about 50 ml and about 200 ml, or the cell culture chamber has a volume of about 180 ml. The use of a low chamber height (less than 5 cm, suitably less than 4 cm, less than 3 cm, or less then 2 cm) allows for effective media and gas exchange in close proximity to the cells. Ports are configured to allow mixing via recirculation of the fluid without disturbing the cells. Larger height static vessels can produce concentration gradients, causing the area near the cells to be limited in oxygen and fresh nutrients. Through controlled flow dynamics, media exchanges can be performed without cell disturbance. Media can be removed from the additional chambers (no cells present) without risk of cell loss.

As described herein, in exemplary embodiments the cassette is pre-filled with one or more of a cell culture, a culture media, a cell wash media if desired, an activation reagent, and/or a vector, including any combination of these. In further embodiments, these various elements can be added later via suitable injection ports, etc.

As described herein, in embodiments, the cassettes suitably further include one or more of a pH sensor 524, a temperature sensor 528, a glucose sensor 530, an oxygen sensor 526, a carbon dioxide sensor 532, a lactic acid sensor/monitor (not shown), and/or an optical density sensor 534. See FIG. 5 for exemplary positions within the flowpath. The cassettes can also include one or more sampling ports and/or injection ports. Examples of such sampling ports 220 and injection ports 222 are illustrated in FIG. 2A, and exemplary locations in the flowpath shown in FIG. 5, and can include an access port for connecting the cartridge to an external device, such as an electroporation unit or an additional media source. FIG. 2A also shows the location of the input 202, reagent warming bag 224 which can be used to warm cell media, etc., and secondary chamber 230.

In embodiments, cassette 102 suitably includes a low temperature chamber, which can include a refrigeration area 226 suitably for storage of a cell culture media, as well as a high temperature chamber, suitably for carrying out activation, transduction and/or expansion of a cell culture. Suitably, the high temperature chamber is separated from the low temperature chamber by a thermal barrier. As used herein "low temperature chamber" refers to a chamber, suitably maintained below room temperature, and more suitably from about 4° C. to about 8° C., for maintenance of cell media, etc., at a refrigerated temperature. The low temperature chamber can include a bag or other holder for media, including about 1 L, about 2 L, about 3 L, about 4 L, or about 5 L of fluid. Additional media bags or other fluid sources can be connected externally to the cassette, and connected to the cassette via an access port.

As used herein "high temperature chamber" refers to chamber, suitably maintained above room temperature, and more suitably maintained at a temperature to allow for cell proliferation and growth, i.e., between about 35-40° C., and more suitably about 37° C. In embodiments, high temperature chamber suitably includes cell culture chamber 206 (also called proliferation chamber or cell proliferation chamber throughout).

In embodiments, tangential flow filter 204 is suitably aligned in cassette 102 so that the tangential flow filter is at an angle of about 3° to about 20°, relative to horizontal, more suitably about 5° to about 15° or about 10°, relative to horizontal (exit end of tangential flow filter 204 located above/higher than input end). Alignment of tangential flow filter 204 at an angle relative to horizontal in which the exit end (i.e. 262) of tangential flow filter is above the input end is desirable for providing the desired flow characteristics to yield improved volume reduction and cell concentration via tangential flow filter 204.

The alignment of the tangential flow filter at an angle between about 3° to about 20°, relative to horizontal, also provides the advantage that cell priming (or gravity settling) can be reduced or avoided. Using such an angle allows the cells tumble out of suspension as they flow down the tangential flow filter.

In embodiments, cassette 102 can also include a cell wash system 512 that is suitably contained within cassette 102 (i.e., within the structure shown in FIG. 2A), and fluidly connected to tangential flow filter 204, or can be connected to other sections within the cassette, depending upon whether cell washing is desired. In embodiments, cell wash system 512 is a container or bag contained within cassette 102 that suitably includes a cell wash media. The cell wash media is suitably used to clean the desired cell population to remove any undesired waste cells or contamination prior to transferring the cell population within the cassette or outside the cassette for further processing or use. Cell wash system 512 can also be included outside of cassette 102.

Cassette 102 can also further optionally include a cell holding chamber 516 (not visible in FIG. 2 as it is located inside cassette 102). FIG. 5 shows an exemplary location of cell holding chamber 516 in the flowpath for the cassette. Cell holding chamber 516 is suitably a reservoir or suitable chamber located within the cassette into which a cell population can be held, either prior to or following tangential flow filtration, as described herein.

In additional embodiments, provided herein is cassette 102 for use in an automated cell engineering system 300, suitably comprising cell culture chamber 206, pumping system 520 fluidly connected to the cell culture chamber, and tangential flow filter 204 fluidly connected to the pumping system. As described herein, the pumping system provides a retentate flow to the tangential flow filter and a permeate flow of the tangential flow filter is controlled by a flow controller. The cassette also further includes satellite volume 550 connected to the tangential flow filter, a fluidics pathway 540 for recirculating the retentate flow back through the tangential flow filter, fixed volume waste collection chamber 510 fluidly connected to the tangential flow filter, and cellular sample output 208 fluidly connected to the tangential flow filter.

Exemplary pore sizes and fiber diameters for use in tangential flow filter 204 are described herein. In embodiments, the tangential flow filter has a pore size of about 0.40 µm to about 0.80 µm and a fiber diameter of about 0.5 mm to about 0.9 mm, including a pore size of about 0.60 µm to about 0.70 µm and a fiber diameter of about 0.70 mm to about 0.80 mm.

Suitable materials for use in tangential flow filter include a polymer, such as but not limited to, poly(ether sulfone), poly(acrylonitrile) and poly(vinylidene difluoride).

In exemplary embodiments, cassette 102 further includes one or more fluidics pathways, wherein the fluidics pathways provide recirculation, removal of waste and homogenous gas exchange and distribution of nutrients to the cell culture chamber without disturbing cells within the cell culture chamber. In embodiments, the cell culture chamber is a flat and non-flexible chamber, having a low chamber height.

As described herein, cassette 102 can further include one or more of a pH sensor 524, a glucose sensor 530, an oxygen sensor 526, a carbon dioxide sensor 532, and/or an optical density sensor 534, and can also include one or more sampling ports.

In embodiments, the tangential flow filter is at an angle of about 3° to about 20°, relative to horizontal, located with cassette 102.

As described herein, the flow controller can be a flow restrictor, an additional pumping system 521, a system having a plurality of tubing, or combinations of such controllers.

Figure 3A:
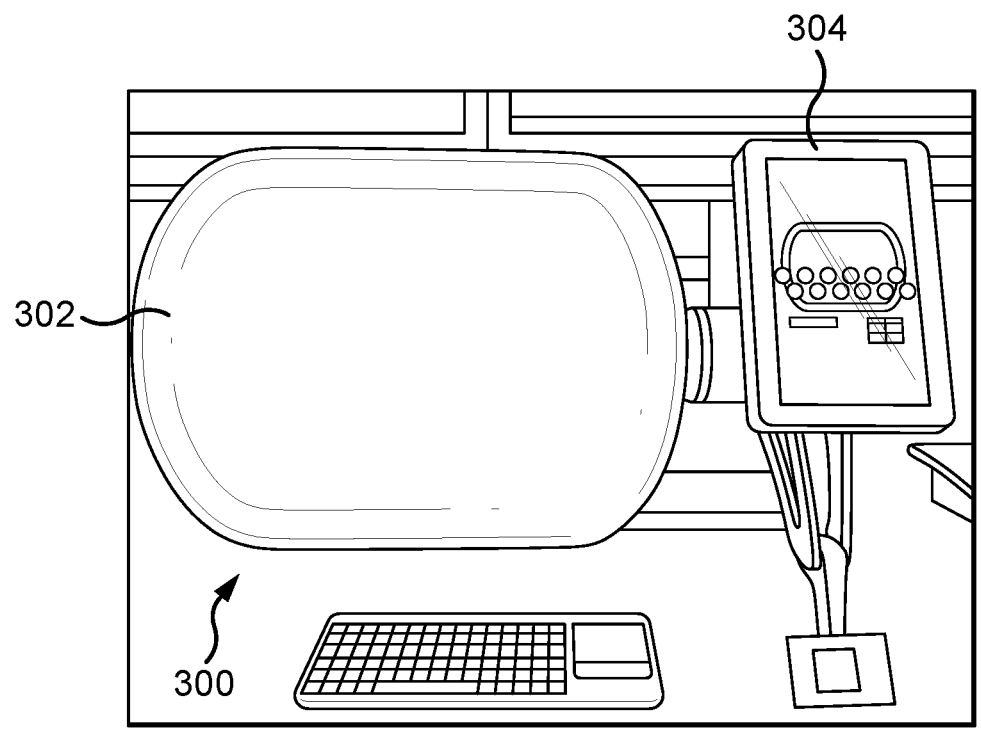
FIGS. 3A and 3B show images of an automated cell engineering system in accordance with embodiments hereof.
Figure 3B:
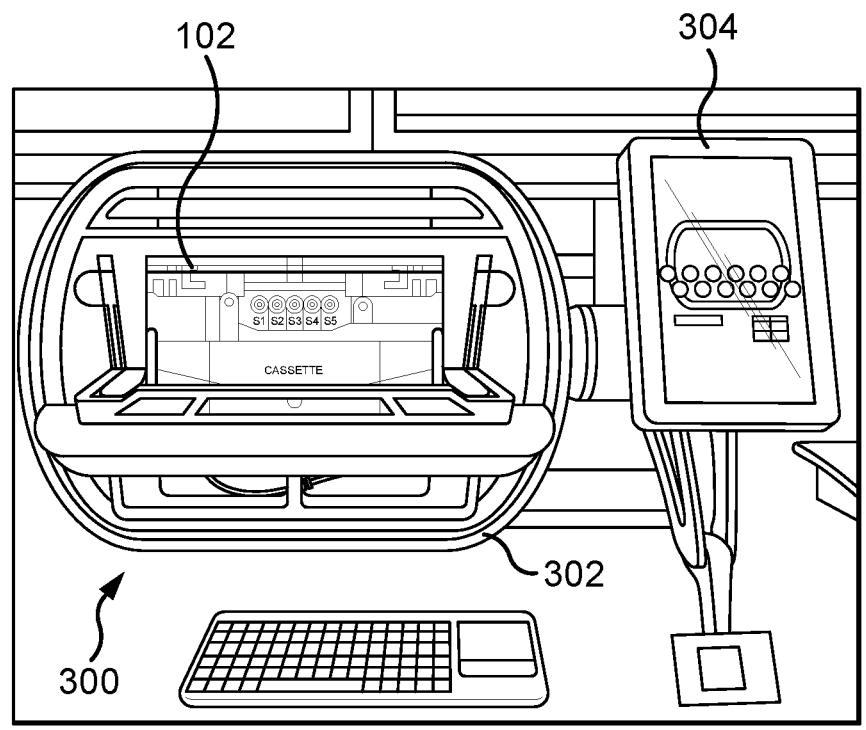

FIGS. 3A-3B show the COCOON® automated cell engineering system 300 with cassette 102 positioned inside (cover of automated cell engineering system opened in FIG. 3B). Also shown is an exemplary user interface, which can include a bar code reader, and the ability to receive using inputs by touch pad or other similar device.

The automated cell engineering systems and cassettes described herein suitably have three relevant volumes, the cell culture chamber volume, the working volume, and the total volume. Suitably, the working volume used in the cassette ranges from 180 mL to 460 mL based on the process step, and can be increased up to about 500 mL, about 600 mL, about 700 mL, about 800 mL, about 900 mL or about 1 L. In embodiments, the cassette can readily achieve $4*10^9$ cells-$10*10^9$ cells. The cell concentration during the process varies from $0.3*10^6$ cells/ml to approximately $10*10^6$ cells/ml. The cells are located in the cell culture chamber, but media is continuously recirculated through additional chambers (e.g., crossflow reservoir and satellite volume) to increase the working volume, as described herein.

Fluidics pathways, including gas exchange lines, may be made from a gas-permeable material such as, e.g., silicone. In some embodiments, the automated cell engineering system recirculates oxygen throughout the substantially non-yielding chamber during the cell production methods. Thus, in some embodiments, the oxygen level of a cell culture in the automated cell engineering system is higher than the oxygen level of a cell culture in a flexible, gas-permeable bag. Higher oxygen levels may be important in the cell culture expansion step, as increased oxygen levels may support increased cell growth and proliferation.

In further embodiments, provided herein is a method of reducing a volume of a cellular sample during automated processing. The method provided herein is described with reference to the flowpath of FIG. 5 for illustrative purposes only, but should not be considered to limit the way in which such a method can be carried out. For example, a cellular sample can be introduced into cassette 102 via input 202. In other embodiments, a cellular sample can already be within cassette 102, for example following a transduction or cell expansion phase, for example in cell culture chamber 206. The cellular sample is introduced 250 into tangential flow filter 204, for example by passing through valve V11. The tangential flow filter has a retentate flow 254 and a permeate flow 252 (see FIG. 2C). As described herein, permeate flow 252 is controlled by flow controller 258 to provide the desired cell concentration and volume reduction. The cellular sample is passed through retentate flow 254, while volume is removed from the cellular sample via permeate flow 252. Suitably, permeate flow 252 is removed to fixed volume waste collection chamber 510 by passing through valves v1 and v13 (though valve v13 can be removed if desired). Once the desired reduction in volume is attained, the cellular sample having the reduced volume is collected, suitably by passing through valves V1 and V10 to output 208. In other embodiments, the cellular sample with the reduced volume can be collected in, for example, cell holding chamber 516, prior to further automated processing or removal from the cassette.

As described herein, retentate flow 254 is suitably recirculated following the removing volume step to repeatedly pass the cellular sample through retentate flow 254. For example retentate flow 254 can pass out of tangential flow filter 204, through valves V1, V12 and V11, and back into tangential flow filter 204.

In embodiments that utilize fixed volume waste collection chamber 510, once a fixed volume of waste is reached, this will also force the cellular sample back through the tangential flow filter (e.g. through valves V14, V12 and V11), but will not allow any additional volume removal, as removing volume suitably stops once the fixed volume waste collection chamber contains a desired volume.

In additional embodiments, following an initial collection of the cellular sample, the sample can be washed using cell wash system 512, and then the volume reduction method can be repeated. Cell wash system 512 can be connected to cell holding chamber 516, for example, via valves V4, and by closing valves V12 and V11, to force the wash solution into the holding chamber.

The methods described herein can further include additional steps, including for example electroporating the cellular sample following collecting after tangential flow filtration. This can occur via an internal (i.e., with cassette 102) or external electroporation system. Additional transduction steps can also be carried out following the collecting after tangential flow filtration.

As described herein, the methods suitably utilize a flow controller that can be a flow restrictor, an additional pumping system 521, a system having a plurality of tubing, or combinations of such controllers.

Figure 4:
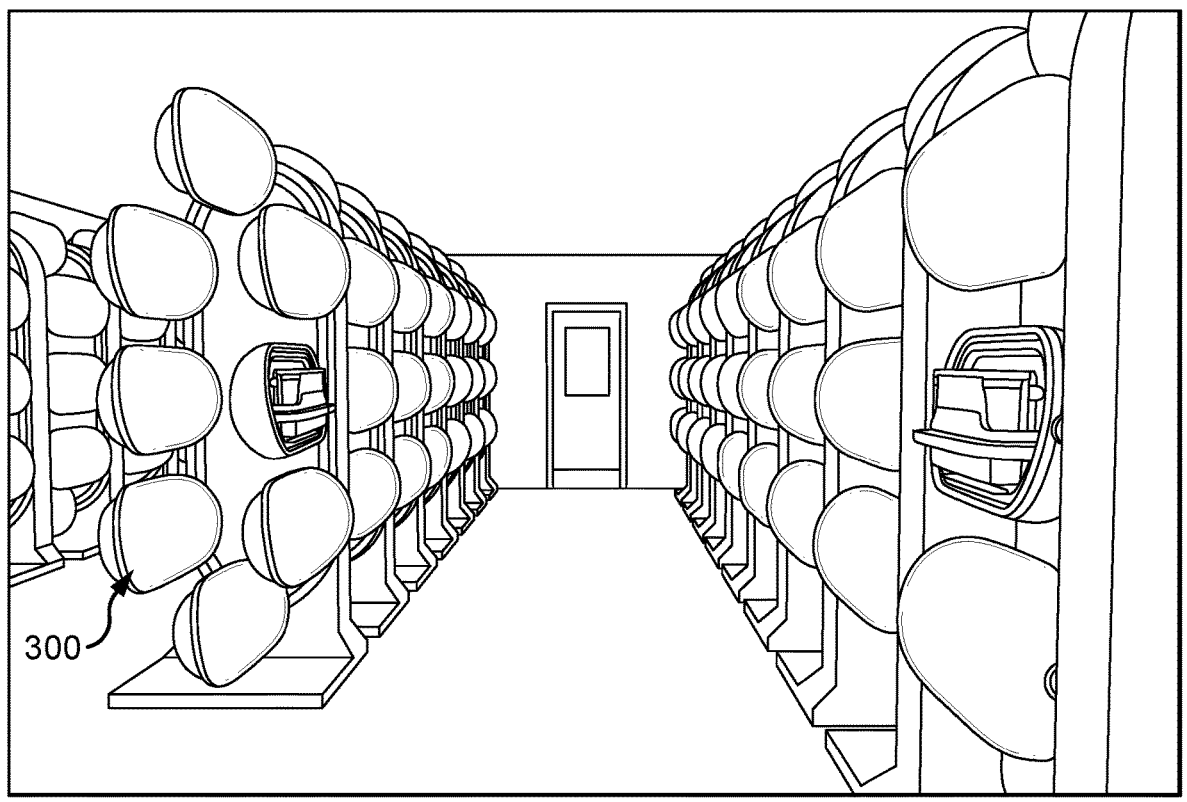
FIG. 4 shows a lab space containing exemplary cell engineering systems as described in embodiments hereof.

In embodiments, the methods and cartridges described herein are utilized in the COCOON® platform (Octane Biotech (Kingston, ON)), which integrates multiple unit operations in a single turnkey platform. Multiple cell protocols are provided with very specific cell processing objectives. To provide efficient and effective automation translation, the methods described utilize the concept of application-specific/sponsor-specific disposable cassettes that combine multiple unit operations—all focused on the core requirements of the final cell therapy product. Multiple automated cell engineering systems 300 can be integrated together into a large, multi-unit operation for production of large volumes of cells or multiple different cellular samples for individual patients (see FIG. 4).

Also illustrated in FIG. 5 are exemplary positioning of various sensors (e.g., pH sensor 524, dissolved oxygen sensor 526), as well as sampling/sample ports and various valves (including bypass check valves 552), as well as one or more fluidic pathways 540, suitably comprising a silicone-based tubing component, connecting the components. As described herein, use of a silicone-based tubing component allows oxygenation through the tubing component to facilitate gas transfer and optimal oxygenation for the cell culture. Also show in FIG. 5 is the use of one or more hydrophobic filters 554 or hydrophilic filters 556, in the flowpath of the cassette.

In additional embodiments, provided herein is an automated cell engineering system 300. As shown in FIGS. 3A and 3B, automated cell engineering system 300 suitably includes an enclosable housing 302, and cassette 102, contained within the enclosable housing. As used herein, "enclosable housing" refers to a structure than can be opened and closed, and within which cassette 102 as described herein, can be placed and integrated with various components such as fluid supply lines, gas supply lines, power, cooling connections, heating connections, etc. As shown in FIGS. 3A and 3B, enclosable housing can be opened (FIG. 3B) to allow insertion of the cassette, and closed (FIG. 3A) to maintain a closed, sealed environment to allow the various automated processes described herein to take place utilizing the cassette.

As described herein, cassette 102 suitably includes cell culture chamber 206, pumping system 520 fluidly connected to the cell culture chamber, and tangential flow filter 204 fluidly connected to the pumping system. As described herein, the pumping system provides a retentate flow to the tangential flow filter, and a permeate flow of the tangential flow filter is controlled by a flow controller. Cassette 102 also suitably includes cellular sample output 208 fluidly connected to the tangential flow filter.

As shown in FIGS. 3A-3B, automated cell engineering system 300 also further includes a user interface 304 for receiving input from a user. User interface 304 can be a touch pad, tablet, keyboard, computer terminal, or other suitable interface, that allows a user to input desired controls and criteria to the automated cell engineering system to control the automated processes and flowpath. Suitably, the user interface is coupled to a computer control system to provide instructions to the automated cell engineering system, and to control the overall activities of the automated cell engineering system. Such instructions can include when to open and close various valves, when to provide media or cell populations, when to increase or decrease a temperature, etc.

Exemplary characteristics of the pore size and fiber diameter of tangential flow filter 204 for use in the automated cell engineering systems are described herein, and in embodiments, the tangential flow filter has a pore size of about 0.40 μm to about 0.80 μm and a fiber diameter of about 0.5 mm to about 0.9 mm, suitably a pore size of about 0.60 μm to about 0.70 μm and a fiber diameter of about 0.70 mm to about 0.80 mm. Suitably polymers for use in the tangential flow filter are described herein, and include poly(ether sulfone), poly(acrylonitrile) and poly(vinylidene difluoride).

In embodiments, the cassette in the automated cell engineering systems further comprises a fixed volume waste collection chamber 510 fluidly connected to the tangential flow filter 204. In embodiments, the cassettes 102 of the automated cell engineering systems 300 further include one or more fluidics pathways 540, wherein the fluidics pathways provide recirculation, removal of waste and homogenous gas exchange and distribution of nutrients to the cell culture chamber 206 without disturbing cells within the cell culture chamber. In embodiments, the cell culture chamber is flat and non-flexible chamber, having a low chamber height. Fluidics pathways can also be included for recirculating the retentate flow back through the tangential flow filter. The cassettes can also include a satellite volume 550 fluidly connected to the tangential flow filter.

In embodiments of the automated cell engineering system, the cassette 102 is pre-filled with culture media, cell wash media, etc. As described herein, in embodiments, the cassette of the automated cell engineering system can further include one or more of a pH sensor 524, a glucose sensor 530, an oxygen sensor 526, a carbon dioxide sensor 532, and/or an optical density sensor 534, and in suitable embodiments, one or more sampling ports.

Exemplary flow controllers are described herein, and include a flow restrictor, an additional pumping system 521, and a system having a plurality of tubing. In embodiments, the tangential flow filter is at an angle of about 3° to about 20°, relative to horizonal, within the cassette.

Automation of unit operations in cell therapy production provides the opportunity for universal benefits across allogeneic and autologous cell therapy applications. In the unique scenario of patient-specific, autologous cell products, and even more emphasized by the clinical success of these therapies, the advantages of automation are particularly compelling due to the significant micro-lot complexities of small batch GMP compliance, economics, patient traceability and early identification of process deviations. The associated emergence of complex manufacturing protocols draws attention to the fact that the value of end-to-end integration of automated unit operations in micro-lot cell production has not been a point of significant study. However, the expected demand for these therapies following their impending approval indicates that implementation of a fully closed end-to-end system can provide a much needed solution to manufacturing bottlenecks, such as hands-on-time and footprint.

Developers of advanced therapies are encouraged to consider automation early in the rollout of clinical translation and scale up of clinical trial protocols. Early automation can influence protocol development, avoid the need for comparability studies if switching from a manual process to an automated process at a later stage, and provide a greater understanding of the longer-term commercialization route.

In exemplary embodiments, the automated cell engineering systems described herein comprise a plurality of chambers, and wherein each of steps of the various methods described herein are performed in a different chamber of the plurality of chambers of the automated cell engineering system, each of the activation reagent, the vector, and cell culture medium are contained in a different chamber of the plurality of the chambers prior to starting the method, and wherein at least one of the plurality of chambers is maintained at a temperature for growing cells (e.g., at about 37° C.) and at least one of the plurality of chambers is maintained at a refrigerated temperature (e.g., at about 4-8° C.).

In embodiments, the automated cell engineering systems described herein are monitored with a temperature sensor 528, a pH sensor 524, a glucose sensor 530, an oxygen sensor 526, a carbon dioxide sensor 532, and/or an optical density sensor 534. Accordingly, in some embodiments, the automated cell engineering system includes one or more of a temperature sensor 528, a pH sensor 524, a glucose sensor 530, an oxygen sensor 526, a carbon dioxide sensor 532, and/or an optical density sensor 534. In additional embodiments, the automated cell engineering system is configured to adjust the temperature, pH, glucose, oxygen level, carbon dioxide level, and/or optical density of the cell culture, based on the pre-defined culture size. For example, if the automated cell engineering system detects that the current oxygen level of the cell culture is too low to achieve the necessary growth for a desired cell culture size, the automated cell engineering system will automatically increase the oxygen level of the cell culture by, e.g., introducing oxygenated cell culture media, by replacing the cell culture media with oxygenated cell culture media, or by flowing the cell culture media through an oxygenation component (i.e., a silicone tubing). In another example, if the automated cell engineering system detects that the current temperature of the cell culture is too high and that the cells are growing too rapidly (e.g., possible overcrowding of the cells may lead to undesirable characteristics), the automated cell engineering system will automatically decrease the temperature of the cell culture to maintain a steady growth rate (or exponential growth rate, as desired) of the cells. In still further embodiments, the automated cell engineering system automatically adjusts the schedule of cell feeding (i.e., providing fresh media and/or nutrients to the cell culture) based on the cell growth rate and/or cell count, or other monitored factors, such as pH, oxygen, glucose, etc. The automated cell engineering system may be configured to store media (and other reagents, such as wash solutions, etc.) in a low-temperature chamber (e.g., 4° C. or −20° C.), and to warm the media in a room temperature chamber or a high-temperature chamber (e.g., 25° C. or 37° C., respectively) before introducing the warmed media to the cell culture.

Additional Exemplary Embodiments

Embodiment 1 is a cassette for use in an automated cell engineering system, comprising a cell culture chamber, a pumping system fluidly connected to the cell culture chamber, a tangential flow filter fluidly connected to the pumping system, wherein the pumping system provides a retentate flow to the tangential flow filter and wherein a permeate flow of the tangential flow filter is controlled by a flow controller, and a cellular sample output fluidly connected to the tangential flow filter.

Embodiment 2 includes the cassette of embodiment 1, wherein the tangential flow filter has a pore size of about 0.40 μm to about 0.80 μm and a fiber diameter of about 0.5 mm to about 0.9 mm.

Embodiment 3 includes the cassette of embodiment 2, wherein the tangential flow filter has a pore size of about 0.60 μm to about 0.70 μm and a fiber diameter of about 0.70 mm to about 0.80 mm.

Embodiment 4 includes the cassette of any one of embodiments 1-3, wherein the tangential flow filter comprises a polymer selected from the group consisting of poly(ether sulfone), poly(acrylonitrile) and poly(vinylidene difluoride).

Embodiment 5 includes the cassette of any one of embodiments 1-4, further comprising a fixed volume waste collection chamber fluidly connected to the tangential flow filter.

Embodiment 6 includes the cassette of any one of embodiments 1-5, further comprising a fluidics pathway for recirculating the retentate flow back through the tangential flow filter.

Embodiment 7 includes the cassette of any one of embodiments 1-6, further comprising a satellite volume fluidly connected to the tangential flow filter.

Embodiment 8 includes the cassette of any one of embodiments 1-7, further comprising one or more fluidics pathways, wherein the fluidics pathways provide recirculation, removal of waste and homogenous gas exchange and distribution of nutrients to the cell culture chamber without disturbing cells within the cell culture chamber.

Embodiment 9 includes the cassette of any one of embodiments 1-8, wherein the cell culture chamber is a flat and non-flexible chamber, having a low chamber height.

Embodiment 10 includes the cassette of any one of embodiments 1-9, further comprising one or more of a pH sensor, a glucose sensor, an oxygen sensor, a carbon dioxide sensor, and/or an optical density sensor.

Embodiment 11 includes the cassette of any one of embodiments 1-10, further comprising one or more sampling ports.

Embodiment 12 includes the cassette of any one of embodiments, wherein the tangential flow filter is at an angle of about 3° to about 20°, relative to horizontal.

Embodiment 13 includes the cassette of any one of embodiments 1-12, wherein the flow controller is a flow restrictor.

Embodiment 14 includes the cassette of any one of embodiments 1-13, wherein the flow controller is an additional pumping system.

Embodiment 15 includes the cassette of any one of embodiments 1-14, wherein the flow controller is a system having a plurality of tubing.

Embodiment 16 is a cassette for use in an automated cell engineering system, comprising a cell culture chamber, a pumping system fluidly connected to the cell culture chamber, a tangential flow filter fluidly connected to the pumping system, wherein the pumping system provides a retentate flow to the tangential flow filter and wherein a permeate flow of the tangential flow filter is controlled by a flow controller, a satellite volume connected to the tangential flow filter, a fluidics pathway for recirculating the retentate flow back through the tangential flow filter, a fixed volume waste collection chamber fluidly connected to the tangential flow filter, and a cellular sample output fluidly connected to the tangential flow filter.

Embodiment 17 includes the cassette of embodiment 16, wherein the tangential flow filter has a pore size of about 0.40 µm to about 0.80 µm and a fiber diameter of about 0.5 mm to about 0.9 mm.

Embodiment 18 includes the cassette of embodiment 17, wherein the tangential flow filter has a pore size of about 0.60 µm to about 0.70 µm and a fiber diameter of about 0.70 mm to about 0.80 mm.

Embodiment 19 includes the cassette of any one of embodiments 16-18, wherein the tangential flow filter comprises a polymer selected from the group consisting of poly(ether sulfone), poly(acrylonitrile) and poly(vinylidene difluoride).

Embodiment 20 includes the cassette of any one of embodiments 16-19, further comprising one or more fluidics pathways, wherein the fluidics pathways provide recirculation, removal of waste and homogenous gas exchange and distribution of nutrients to the cell culture chamber without disturbing cells within the cell culture chamber.

Embodiment 21 includes the cassette of any one of embodiments 16-20, wherein the cell culture chamber is a flat and non-flexible chamber, having a low chamber height.

Embodiment 22 includes the cassette of any one of embodiments 16-21, further comprising one or more of a pH sensor, a glucose sensor, an oxygen sensor, a carbon dioxide sensor, and/or an optical density sensor.

Embodiment 23 includes the cassette of any one of embodiments 16-22, further comprising one or more sampling ports.

Embodiment 24 includes the cassette of any one of embodiments 16-23, wherein the tangential flow filter is at an angle of about 3° to about 20°, relative to horizontal.

Embodiment 25 includes the cassette of any one of embodiments 16-24, wherein the flow controller is a flow restrictor.

Embodiment 26 includes the cassette of any one of embodiments 16-25, wherein the flow controller is an additional pumping system.

Embodiment 27 includes the cassette of any one of embodiments 16-26, wherein the flow controller is a system having a plurality of tubing.

Embodiment 28 is a method of reducing a volume of a cellular sample during automated processing, the method comprising introducing a cellular sample into a tangential flow filter having a retentate flow and a permeate flow, wherein the permeate flow is controlled by a flow controller, passing the cellular sample through the retentate flow of the tangential flow filter, removing volume from the cellular sample via the permeate flow to a fixed volume waste collection chamber, and collecting the cellular sample having the reduced volume.

Embodiment 29 includes the method of embodiment 28, further comprising recirculating the retentate flow following the removing volume step to repeatedly pass the cellular sample through the retentate flow.

Embodiment 30 includes the method of any one of embodiments 28-29, wherein the removing volume stops once the fixed volume waste collection chamber contains a desired volume.

Embodiment 31 includes the method of any one of embodiments 28-30, further comprising washing the cellular sample following the collecting, and repeating steps (a)-(d) of the method.

Embodiment 32 includes the method of any one of embodiments 28-31, further comprising electroporating the cellular sample following the collecting.

Embodiment 33 includes the method of any one of embodiments 28-32, wherein the flow controller is a flow restrictor.

Embodiment 34 includes the method of any one of embodiments 28-33, wherein the flow controller is an additional pumping system.

Embodiment 35 includes the method of any one of embodiments 28-34, wherein the flow controller is a system having a plurality of tubing.

Embodiment 36 is an automated cell engineering system, comprising an enclosable housing, a cassette contained within the enclosable housing, the cassette comprising a cell culture chamber, a pumping system fluidly connected to the cell culture chamber, a tangential flow filter fluidly connected to the pumping system, wherein the pumping system provides a retentate flow to the tangential flow filter and wherein a permeate flow of the tangential flow filter is controlled by a flow controller, and a cellular sample output fluidly connected to the tangential flow filter, and a user interface for receiving input from a user.

Embodiment 37 includes the automated cell engineering system of embodiment 36, wherein the tangential flow filter has a pore size of about 0.40 µm to about 0.80 µm and a fiber diameter of about 0.5 mm to about 0.9 mm.

Embodiment 38 includes the automated cell engineering system of embodiment 37, wherein the tangential flow filter has a pore size of about 0.60 µm to about 0.70 µm and a fiber diameter of about 0.70 mm to about 0.80 mm.

Embodiment 39 includes the automated cell engineering system of any one of embodiments 36-38, wherein the tangential flow filter comprises a polymer selected from the group consisting of poly(ether sulfone), poly(acrylonitrile) and poly(vinylidene difluoride).

Embodiment 40 includes the automated cell engineering system of any one of embodiments 36-39, further comprising a fixed volume waste collection chamber fluidly connected to the tangential flow filter.

Embodiment 41 includes the automated cell engineering system of any one of embodiments 36-40, further comprising a fluidics pathway for recirculating the retentate flow back through the tangential flow filter.

Embodiment 42 includes the automated cell engineering system of any one of embodiments 36-41, further comprising a satellite volume fluidly connected to the tangential flow filter.

Embodiment 43 includes the automated cell engineering system of any one of embodiments 36-42, further comprising one or more fluidics pathways, wherein the fluidics pathways provide recirculation, removal of waste and homogenous gas exchange and distribution of nutrients to the cell culture chamber without disturbing cells within the cell culture chamber.

Embodiment 44 includes the automated cell engineering system of any one of embodiments 36-43, wherein the cell culture chamber is a flat and non-flexible chamber, having a low chamber height.

Embodiment 45 includes the automated cell engineering system of any one of embodiments 36-44, further comprising one or more of a pH sensor, a glucose sensor, an oxygen sensor, a carbon dioxide sensor, and/or an optical density sensor.

Embodiment 46 includes the automated cell engineering system of any one of embodiments 36-45, further comprising one or more sampling ports.

Embodiment 47 includes the automated cell engineering system of any one of embodiments 36-46, wherein the tangential flow filter is at an angle of about 3° to about 20°, relative to horizontal.

Embodiment 48 includes the automated cell engineering system of any one of embodiments 36-47, further comprising a computer control system, wherein the user interface is coupled to the computer control system to provide instructions to the automated cell engineering system.

Embodiment 49 includes the automated cell engineering system of any one of embodiments 36-48, wherein the flow controller is a flow restrictor.

Embodiment 50 includes the automated cell engineering system of any one of embodiments 36-48, wherein the flow controller is an additional pumping system.

Embodiment 51 includes the automated cell engineering system of any one of embodiments 36-48, wherein the flow controller is a system having a plurality of tubing.

EXAMPLES

Example 1—Tangential Flow Filtration in COCOON™ System

Tangential flow filtration (TFF) for cell therapy applications can be used to separate, clarify, recover and collect cells from a post-harvest suspension fluid, prior to formulation. A traditional TFF process consists of two steps; 1) volume reduction and 2) diafiltration. During the volume reduction step the bulk volume (cells in harvest reagent and culture media) is constantly removed via filtration through the permeate side of the filter until a desired cell concentration is reached in the processing bag. During diafiltration, the concentrated cell suspension solution is replaced with a formulation buffer and residual proteins and contaminants that are undesirable in the final solution are reduced to acceptable levels. The final cell suspension will be at a cell concentration and in a buffer that is ready for formulation. Tangential flow filters are preferred over standard filters as they can reduce fluid volume while preventing clogging and avoiding cell damage. The cells are also easier to retrieve as they are not compressed against the filter.

TFF filters are single use and disposable so they can be easily implemented into a cassette to perform operations in a closed and automated manner. A completely closed system allows the process to be performed aseptically, as cell therapy products cannot be terminally sterilized or filtered. A fully disposable system eliminates cross-contamination risks and reduces cleaning requirements. To increase the functionality of the COCOON™, a cassette is provided with an integrated tangential flow filter. This example details the development of a TFF system to concentrate and wash cells in an automated system for cell therapy applications.

Methods
Tangential Flow Filtration in COCOON™ Cassette

TFF systems for cell concentration typically have two pumps, one to control the feed flow rate and one to control the permeate (i.e. waste) flow rate. The flow rate of each pump is typically determined based on optimizing transmembrane pressure. If the pressure differential is too high or too low, it can cause either nothing to pass through the filter, thus making the system ineffective, or it can lead to clogging. The COCOON™ generally operates on a single pump, and without pressure sensors, so the conventional methods of filtering via TFF do not apply.

Experiments were run with TFF filters installed in either a COCOON™ cassette or cassette-like pathway. As described herein, the cassette pathway contains an expansion chamber for cell culture, satellite bags or L-shaped chamber for cell processing, a TFF to remove excess media, and a waste bag to collect the excess media. The COCOON™ cassette suitably recirculates up to 450 mL of culture media in its culture chamber. Additional media volume beyond the 180 mL capacity of the 260 $cm^2$ proliferation chamber is provided from various satellite reservoirs of the COCOON™ cassette. The additional media from these satellite reservoirs can be recirculated within the culture portion of the disposable cassette to provide fresh nutrients and remove waste products from cells in the proliferation chamber.

To generate a pressure differential, a flow restrictor was used in the permeate line. Based on experimental optimization, an ideal permeate flow rate was selected that avoided clogging, maximized cell recovery and minimized time for the volume reduction. In parallel with this, a wide range of filters were tested to understand the impact of fiber diameter, fiber area, number of fibers, total surface area, cell type, retentate flow rate, pore size and filter material.

Fixed Volume Waste Container

Several experiments also utilized a fixed volume waste container. Cassettes typically have a flexible waste bag located in the fluids reservoir. This bag has the capacity to expand, potentially leading to complete drain of the satellite bag and TFF in certain situations. A complete drain of the filter leads to irreversible loss of cells due to trapping on the filter membrane. To limit the capacity of the waste bag, it can be held between two rigid layers of plastic with fixed separation in the fluids reservoir. The bag fills to a fixed volume, at which point the pressure in the bag is such that recirculation through the satellite bag/TFF continues, without further delivery of fluid to waste.

Custom Filter to Concentrate Peripheral Blood Mononuclear Cells (PBMC)

Initial cell concentration experiments revealed desired properties of a tangential flow filter, such as increased surface area and a large pore size. The Spectrum Labs P-OCTA01-04-N filter is a custom designed filter to meet these requirements and fit inside a Cocoon cassette. Properties include:
mPES membrane
Fiber diameter=0.75
Pore size=0.65 μm
Number of Fibers=18
Lumen=13 cm total length
Surface area=57 $cm^2$ This filter was evaluated, optimized, and then used in proof-of-concept electroporation integration studies.

TFF Volume Reduction Using Custom Filter

Initial studies of the custom filter were performed without the COCOON™. The KrosFlo® Research 2i TFF System (Spectrum Labs) was used to monitor feed, retentate, permeate and transmembrane pressures during cell processing. Only one pump that controls the flow rate of the feed line was utilized (unless mentioned otherwise) to mimic the COCOON™ instrument capabilities. A 20 gauge, 0.024" I.D./0.036" O.D., flow restrictor from Nordson EFD, which was added to the end of the permeate line to mimic previously optimized TFF procedures. By using this system, a cell suspension of 100 mL was concentrated down to 10-20 mL. TFF was performed on the benchtop at room temperature. Transmembrane pressure is defined as:

$$TMP = \frac{P_{feed} + P_{retentat}}{2} - P_{permeate}$$

PBMC Culture $1 \times 10^8$ PBMCs were stimulated with $1 \times 10^8$ CD3+:CD28+ Dynabeads (Invitrogen) and expanded in Complete T-cell Media comprised of X-VIVO 15 media (Lonza) supplemented with 5% Human Serum A/B (Sigma) and 10 ng/mL IL-2 (Peprotech) using multiple GREX 100 (Wilson Wolf) culture vessels for up to 10 days. To accommodate high viscosity serum that can clog the filter, a pre-wash protocol in the COCOON™ has been defined to first reduce the concentration of the serum prior to the volume reduction using the TFF process. Test concentrations of cells were transferred to 250 mL conical vials and either centrifuged or allowed to settle in 37° C. incubators with 5% $CO_2$ in air humidified for 2-4 hrs. The supernatant of the settled cell suspension was reduced to 10 mL and excess supernatant discarded. The appropriate media was added to the concentrated cell suspension for a final volume of 100 mL.

Analysis

Counts were performed in duplicate using the Nucleocounter NC-200 (Chemometec) on the pre-diluted cell culture, the diluted culture and the final concentrated cell suspension. Volumes were measured using a serological pipette and KrosFlo scales before and after TFF. Residual testing samples were obtained from the initial culture pre-dilution, supernatant pre-TFF, and final concentrated cell suspension post TFF. A Human Serum ELISA Kit (Bethyl Laboratories) was used to determine the percentage of serum remaining post dilution and concentration. FACS analysis was performed on control cells and TFF concentrated cell suspensions for CD4+ and CD8+ expression.

Successful demonstration of TFF volume reduction was defined as follows:

≥85% recovery of cells post TFF
≤10% decrease in cell viability post TFF
≤10%, Residual human serum of the initial concentration post TFF (for electroporation studies)

Results

Evaluation of Tangential Flow Filters

A wide variety of filters were tested to understand the impact of various filter parameters. Fiber diameter, fiber area, number of fibers, total surface area, retentate flow rate, pore size, and filter material all play a role in the effectiveness of the filter in reducing the volume of a cell suspension. The results were also impacted by the solution (e.g. media type, and the type of serum) as well as the cell type (i.e. size), the number of cells, the cell concentration and the target final volume. Hydrostatic pressure was also influential and so the flow restrictor had to be adjusted depending on hydrostatic pressure. Most runs used human mesenchymal stem cells (hMSC) as the tested cell type.

To accommodate variability in the amount of permeate flow, a non-flexible waste container was used with a fixed volume. For example, if 100 mL needed to be removed from the total volume, a waste container of exactly 100 mL was used. The duration of flow could be set based on the slowest permeate flow. A by-pass loop was placed on either side of the pump tube with an in-line high pressure check valve. If the waste filled before the pumping time was complete, the by-pass line was activated, causing the fluid to pump in a circle, thus ending the TFF process. This approach achieved very consistent flow rate to waste as demonstrated in Table 1. For additional control, a level sensor can be integrated into the COCOON™ to monitor the fluid level in the non-flexible container.

TABLE 1

Fixed Volume Waste Container Run Summary

| Starting Number (Live # M) | Suspension Volume (mL) | Cell Viability (%) | Waste Volume (mL) | Concentrated Volume (Including 8 mL rinse) (mL) | Final Viability (%) | Change in Viability (%) | Post-Collection Viability Control (%) | Total Cell Recovery (Live # M) | Calculated Overall Efficiency (%) | Control Post-Test a % of starting population (%) | Calculated Overall Efficiency adjusted for control (%) |
|---|---|---|---|---|---|---|---|---|---|---|---|
| 40 | 160 | 97.7 | 123 | 35.7 | 92.2 | -5.5 | — | 29.7 | 74.3 | — | — |
| 40 | 160 | 95 | 117 | 35.8 | 93.1 | -1.9 | 94.8 | 29.2 | 72.9 | 89.8 | 83 |
| 38 | 160 | 94.9 | 117 | 38.5 | 93.8 | -1.1 | 94.9 | 32.7 | 86.8 | 94.9 | 82 |
| 40 | 160 | 95.1 | 119 | 34.1 | 90.2 | -4.9 | 96.6 | 29.3 | 73.0 | 88.7 | 83 |
| 39 | 160 | 94.4 | 120 | 34.9 | 88.8 | -5.6 | 92.9 | 27.7 | 70 | 86.3 | 80 |
| 38 | 160 | 93.7 | 120 | 35.7 | 89.8 | -3.9 | 92.5 | 27.9 | 74 | 88.8 | 82 |
| 41 | 160 | 96 | 124 | 35.3 | 89.8 | -6.2 | 96.3 | 31.2 | 76.4 | 91.2 | 83 |
| 37 | 160 | 95.6 | 120 | 43 | 94.1 | -1.2 | 94.7 | 29.5 | 80 | 88.2 | 89 |
| 38 | 160 | 98.4 | 125 | 36.2 | 95.3 | -3.1 | 97.2 | 28.7 | 76 | 92.7 | 82 |
| 38 | 160 | 97.8 | 126 | 30.7 | 94.5 | -3.3 | 95.1 | 30.7 | 81.3 | 97.8 | 83 |

Evaluation and Optimization of Custom Tangential Flow Filter

The results of the testing of the various tangential flow filters revealed desirable conditions. A custom filter, Spectrum Labs P-OCTA01-04-N, met these specifications, but testing and optimization was needed. We wanted to ensure that the filter was working correctly and initially decouple any limitations of the COCOON™ system; therefore, we used a Spectrum Labs TFF system to evaluate the filter.

Figures 6A, 6B:
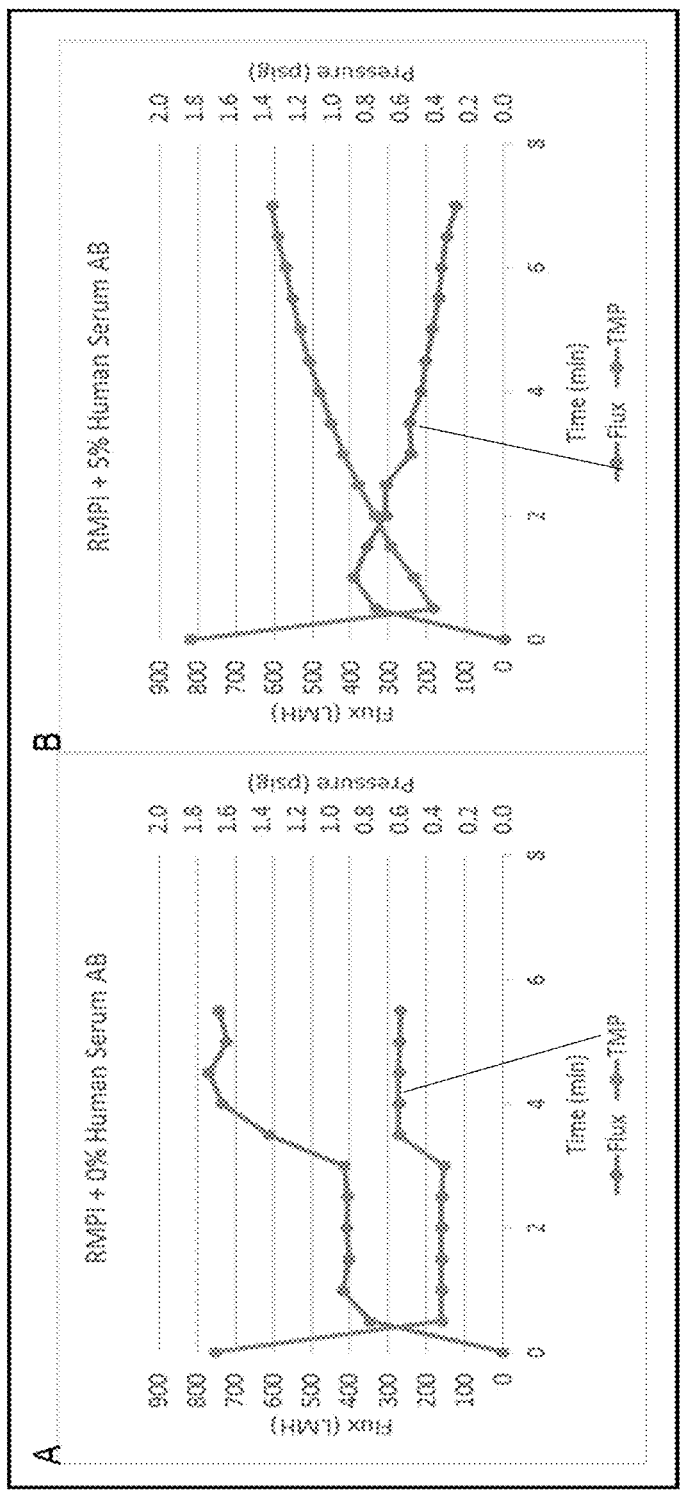
FIG. 6A-6B show the effect of serum on tangential flow filtration, in accordance with embodiments hereof.

Acellular runs were initiated to receive initial working parameters of the filter. When the volume of RPMI media was reduced, there was a constant transmembrane pressure (TMP) and flux through the filter (FIG. 6A). However, if serum is added to the RMPI, TMP increases and flux decrease over time (FIG. 6B). This is a sign that the filter is clogging from the proteins in the serum.

Figures 7A, 7B, 7C:
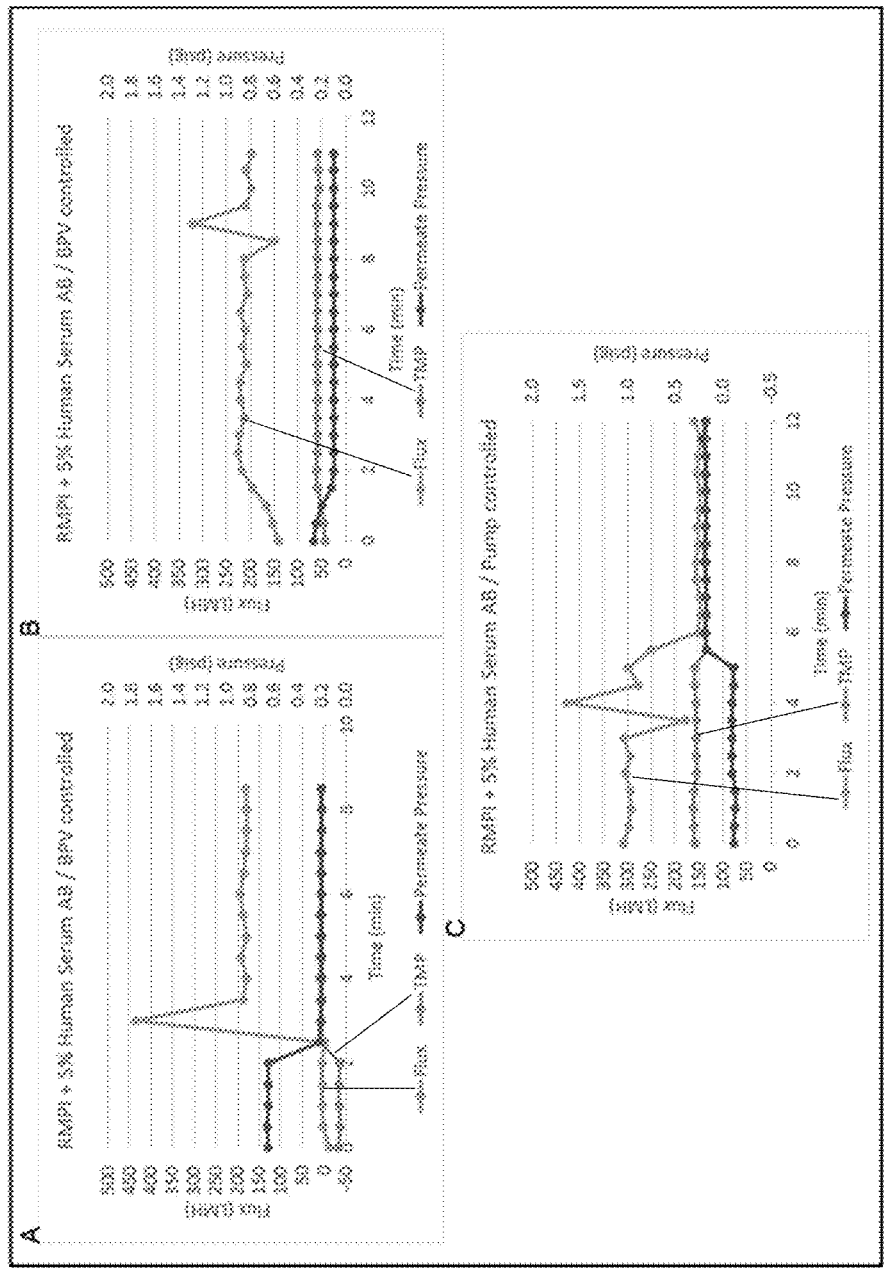
FIGS. 7A-7C show the use of permeate control to reduce the clogging of the tangential flow filter in accordance with embodiments hereof.

To control the clogging from the serum, either an automated backpressure valve (FIGS. 7A and 7B) or secondary pump (FIG. 7C) was added to the permeate line. The automated backpressure valve is able to control the permeate pressure after 3 minutes of volume reduction. The secondary pump controlled the permeate flowrate to 20 ml/min initially and then 10 ml/min after 5.5 minutes. In both cases of permeate control, there was a mostly constant flux, permeate pressure, and TMP. The results indicate that controlling the pressure on the TFF permeate line in the COCOON™, provides control over filter clogging.

Figures 8A, 8B:
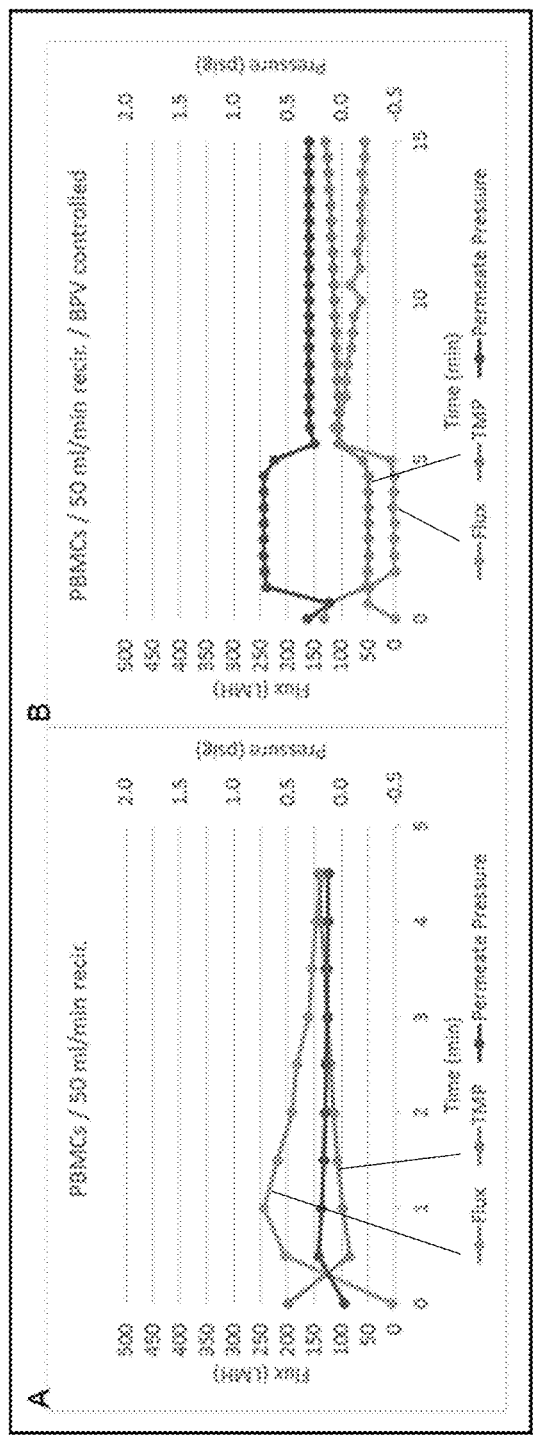
FIGS. 8A-8B show volume reduction of peripheral blood mononuclear cells (PBMC) using tangential flow filtration in accordance with embodiments hereof.
Figures 9A, 9B, 9C, 9D:
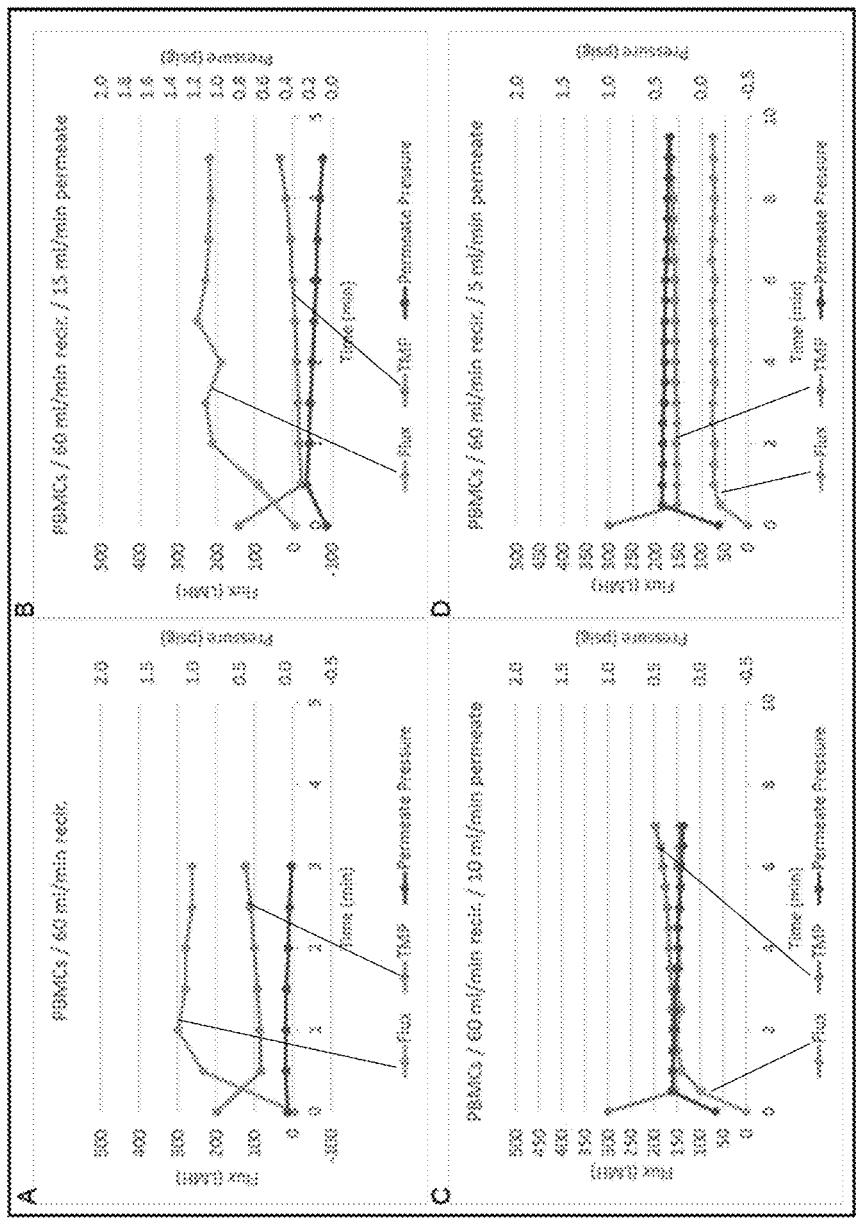
FIGS. 9A-9D show permeate pump optimization during tangential flow volume reduction of PMBCs in accordance with embodiments hereof.

Similar trends are seen with the volume reduction of PBMC suspensions without serum (FIGS. 8A and 8B). The addition of a backpressure control valve on the permeate helps stabilize flux, permeate pressure and TMP. This further confirms the need for permeate control.

In order to receive the greatest cell recovery without significant loss in viability, process parameters are optimized. The first parameter examined is the permeate pressure via the permeate control pump. While concentrating PMBC+0% serum suspensions, the recirculation pump was set to 60 mL/min and the permeate control pump was set to either 0, 5, 10, or 15 mL/min (FIGS. 9A-9D). Speed of the permeate pump appeared to have little effect on the flux, TMP or permeate pressure. 15 mL/min was chosen for the following experiments as this will lead to the quickest TFF duration.

Recirculation flow rate was also examined. PBMCs in a 0% serum suspension were concentrated by TFF with the permeate pump at 15 mL/min and the recirculation flow rate at either 60 mL/min and 70 mL/min (Table 2). There was a larger recovery of cells with a flowrate of 70 mL/min.

TABLE 2

Tangential Flow Filtration Concentration of PMBCs with 0% Serum for Permeate Control

| Trial | Recirculation Flow rate (mL/min) | Initial Volume (mL) | Final Volume (mL) | Final Viability (%) | Initial cell count | % Recovery |
|---|---|---|---|---|---|---|
| 1 | 60 | 103 | 16 | 93 | 1.8E9 | 78.6 |
| 2 | 70 | 100 | 15.5 | 94 | 1.5E9 | 95.5 |
| 3 | 70 | 100 | 15.5 | 96 | 1.5E9 | 95.5 |

PBMCs in a 0% serum suspension were concentrated by TFF with a flow restrictor on the permeate line and a recirculation flow rate of 70 mL/min (Table 3). The average recovery was approximately 89% with viabilities greater than 80%.

TABLE 3

Tangential Flow Filtration Concentration of PMBCs with 0% Serum and Flow Restrictor

| Trial | Initial Volume (mL) | Final Volume (mL) | Initial Viability (%) | Final Viability (%) | Initial cell count | % Recovery |
|---|---|---|---|---|---|---|
| 1 | 101 | 20 | 97 | 96 | 2.2E9 | 85 |
| 2 | 100 | 17.8 | 96 | 96 | 1.9E9 | 93 |
| 3 | 103 | 18 | 96 | 96 | 2.8E9 | 93 |
| 4 | 100 | 20 | 96 | 95 | 2.6E9 | 96.6 |
| 5 | 104 | 17.5 | 90 | 84 | 3.4E9 | 76 |
| average | | | | 93.4 | | 88.7 |

Many cellular therapies use serum, and in some instances, it may not be possible to remove serum prior to TFF. PBMCs in a 5% serum suspension were concentrated by TFF with a flow restrictor on the permeate line and the recirculation flow of 70 mL/min (Table 4). The average recovery was approximately 86% with viabilities greater than 80%.

TABLE 4

Tangential Flow Filtration Concentration of PMBCs with 5% Serum and Flow Restrictor

| Trial | Initial Volume (mL) | Final Volume (mL) | Initial Viability (%) | Final Viability (%) | Initial cell count | % Recovery |
|---|---|---|---|---|---|---|
| 1 | 100 | 17.5 | 96 | 98 | 1.8E9 | 95 |
| 2 | 100 | 20.3 | 97 | 79 | 4.5E9 | 75.7 |
| 3 | 100 | 20.5 | 97 | 90 | 2.96E9 | 89.5 |
| 4 | 100 | 19.5 | 97 | 85 | 2.4E9 | 84.4 |
| average | | | | 87.5 | | 86 |

Cell Concentration in the COCOON™ Cassette Via TFF for Electroporation

Figure 10A:
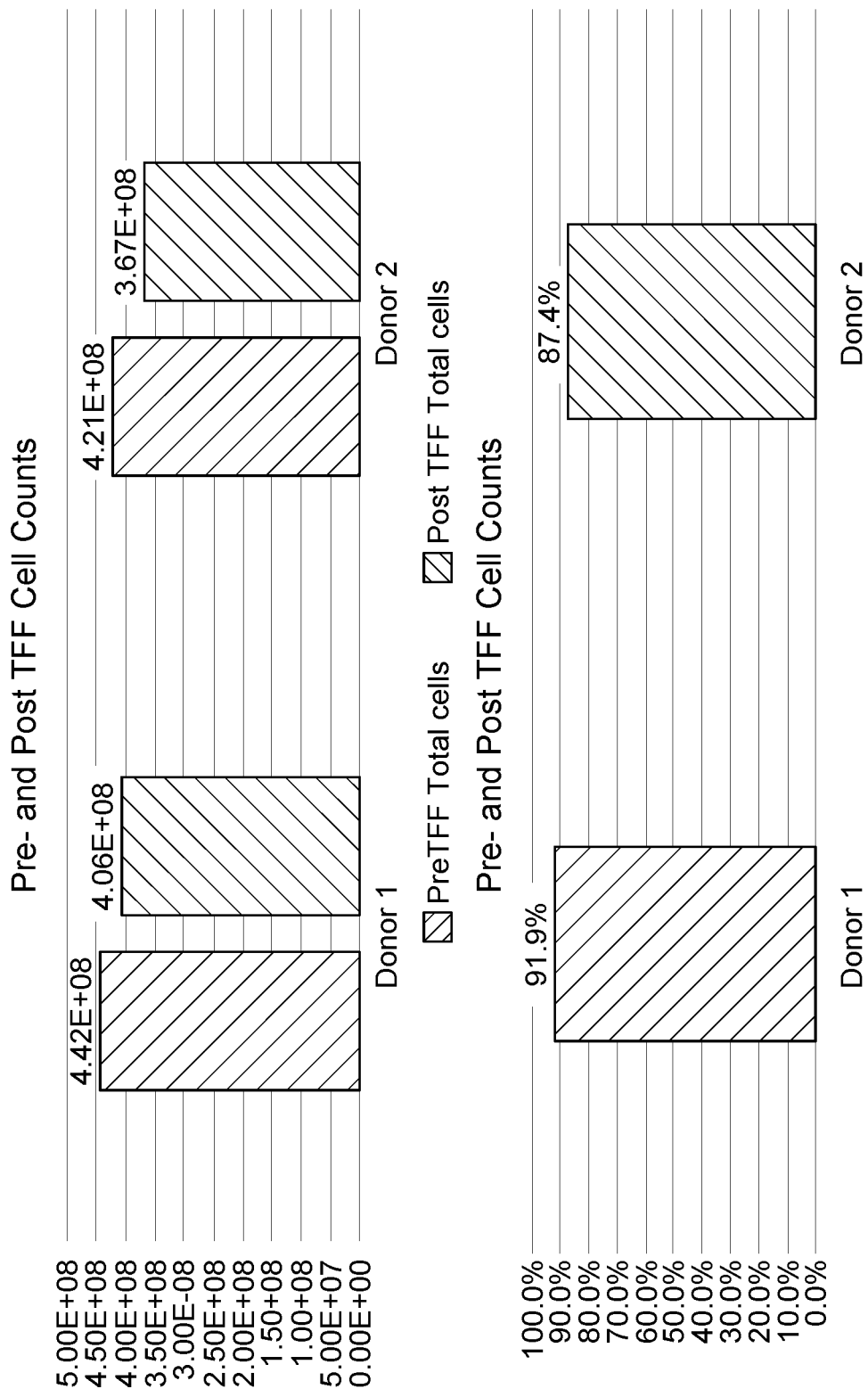
FIG. 10A shows cell recovery post tangential flow filtration, in accordance with embodiments hereof.
Figure 10B:
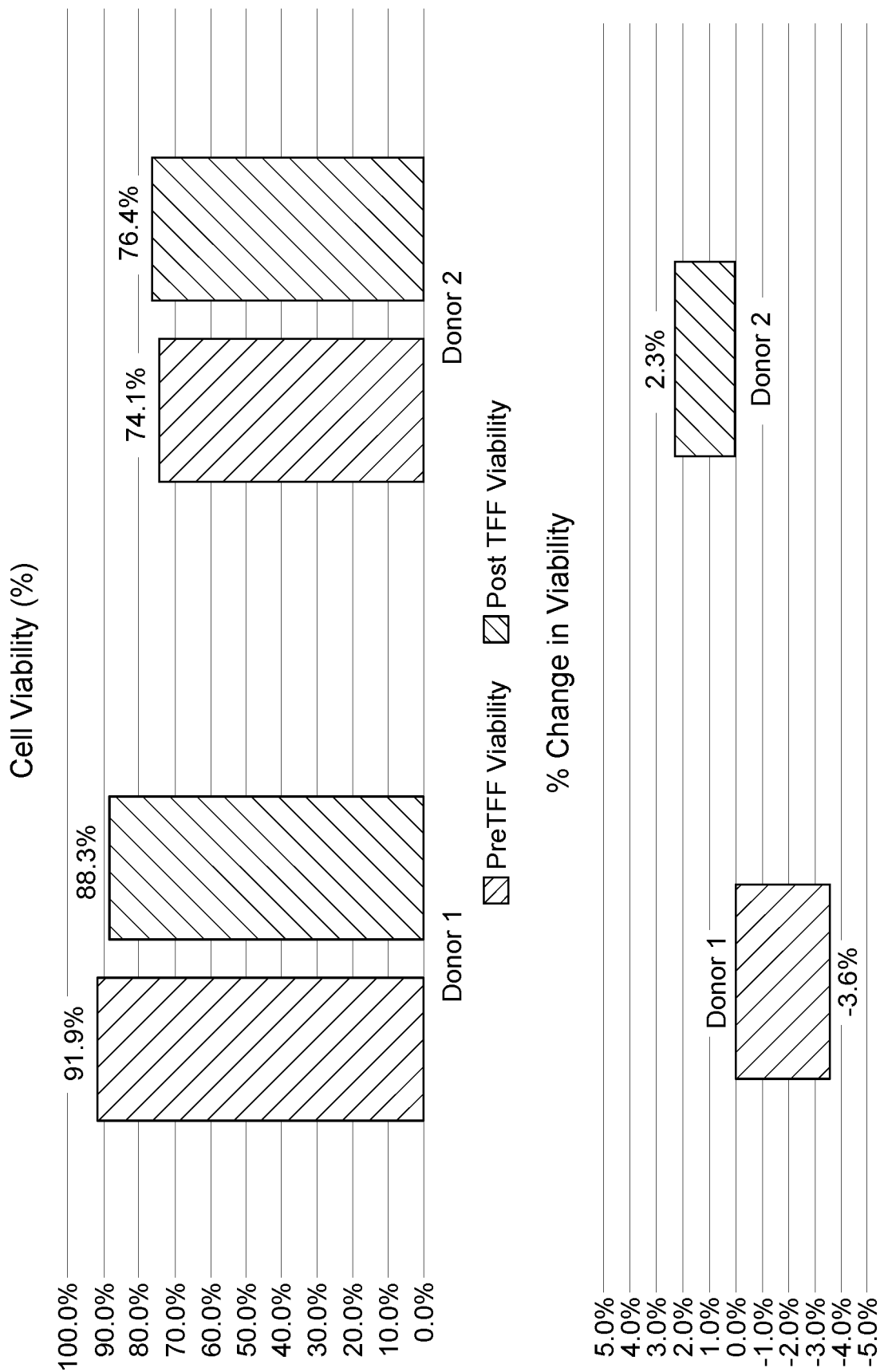
FIG. 10B shows cell viability pre- and post-tangential flow filtration, in accordance with embodiments hereof.

Cell wash and concentration is not only useful prior to downstream processing of a product; it can also be utilized mid-automated process for certain unit operations such as electroporation. Before cells are added to an electroporation unit, cells are suitably concentrated to <10 mL, and residuals washed out. For a proof-of-concept, cells from two donors were concentrated by settling to a 10 mL volume with $4.4 \times 10^8$ and $4.2 \times 10^8$ total viable cells. These two cell suspensions were then diluted with 90 mL of supplemented Nucleofector™ Solution (NFS) and concentrated to 10 mL using TFF. Cell recovery post TFF concentration was 92% and 87% (FIG. 10A). Cell viability prior to transfection was 92% and 74% and decreased by less than 5% post TFF (FIG. 10B).

In both runs, 6% and 8% of the initial culture supernatant was detected in the final TFF concentrated cell suspension (Table 5).

TABLE 5

Percentage of detectable human serum A/B in the original culture supernatant, post diluted and concentrated TFF permeate, and final cell suspension supernatant post TFF.

| Sample ID | Human Serum Concentration of Initial Culture (ng/mL) | Human Serum Concentration Pre-TFF (ng/mL) | Human Serum Concentration Pre-TFF (% of initial) | Human Serum Concentration Post TFF (ng/mL) | Human Serum Concentration Post TFF (% of initial) |
|---|---|---|---|---|---|
| Donor 1 | 4.98E+6 | 2.19E+5 | 4% | 2.8E+5 | 6.00% |
| Donor 2 | 4.28E+6 | 3.48E+5 | 9% | 3.30E+5 | 8.20% |

Figure 11:
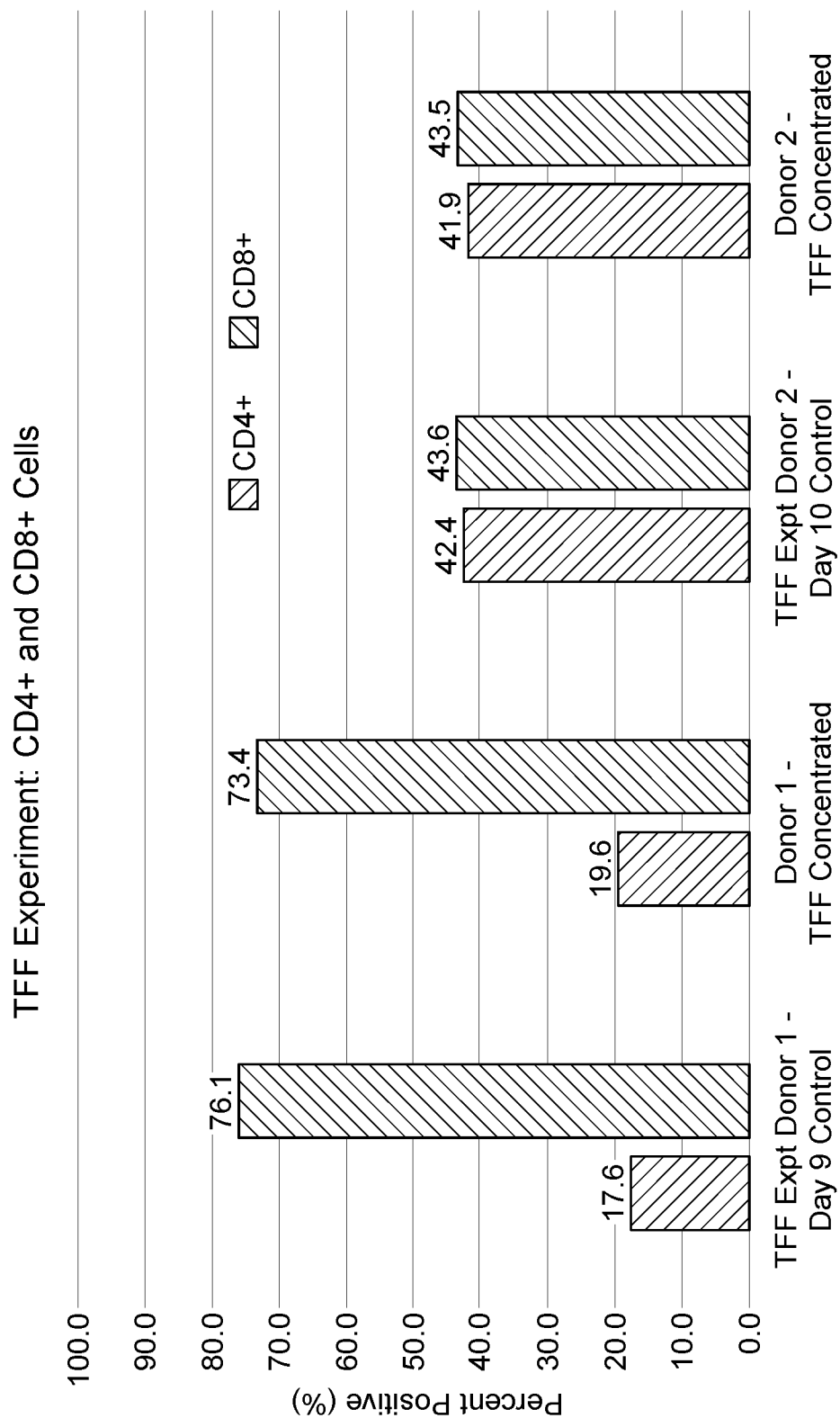
FIG. 11 shows CD4+ and CD8+ expression in control and TFF cell suspensions.

There was no difference in CD4+:CD8+ profiles post TFF compared to the control culture that was not concentrated by TFF (FIG. 11).

These results demonstrate the use of TFF in the washing and concentration of cells prior to in-process transfection.

CONCLUSION

Wash and concentration via Tangential Flow Filtration can be suitably carried out using the COCOON™ system. TFF allows processes to remain closed and automated and fits within the confines of a COCOON™ disposable cassette. TFF can concentrate cell suspensions <20 ml and recover >85% of cells through the system.

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

The invention claimed is:

1. A cassette for use in an automated cell engineering system, comprising:
   (a) a cell culture chamber;
   (b) a pumping system fluidly connected to the cell culture chamber;
   (c) a tangential flow filter fluidly connected to the pumping system, wherein the pumping system provides a retentate flow to the tangential flow filter and wherein a permeate flow of the tangential flow filter is controlled by a flow controller; and
   (d) a cellular sample output fluidly connected to the tangential flow filter,
   wherein (a)-(d) are self-contained and removable, and the cassette comprises a cell culture, a culture media, a cell wash media, an activation reagent, and/or a vector,
   wherein the tangential flow filter is at an angle of about 3° to about 20° relative to the horizontal such that an exit end of the tangential flow filter is disposed vertically above an input end of the tangential flow filter, and
   wherein the cassette is contained within an enclosable housing of the automated cell engineering system.

2. The cassette of claim 1, wherein the tangential flow filter has a pore size of about 0.40 µm to about 0.80 µm and a fiber diameter of about 0.5 mm to about 0.9 mm.

3. The cassette of claim 2, wherein the tangential flow filter has a pore size of about 0.60 µm to about 0.70 µm and a fiber diameter of about 0.70 mm to about 0.80 mm.

4. The cassette of claim 1, wherein the tangential flow filter comprises a polymer selected from the group consisting of poly(ether sulfone), poly(acrylonitrile) and poly(vinylidene difluoride).

5. The cassette of claim 1, wherein the cell culture chamber is maintained at a temperature to allow for cell proliferation and growth.

6. The cassette of claim 1, wherein the cell culture chamber is monitored with a temperature sensor contained within the self-contained, removable cassette.

7. The cassette of claim 1, further comprising one or more fluidics pathways, wherein the fluidics pathways provide recirculation, removal of waste, homogeneous gas exchange, and distribution of nutrients to the cell culture chamber without disturbing cells within the cell culture chamber.

8. The cassette of claim 1, further comprising a pH sensor, a glucose sensor, an oxygen sensor, a carbon dioxide sensor, and/or an optical density sensor.

9. The cassette of claim 1, further comprising one or more sampling ports.

10. The cassette of claim 1, wherein the flow controller is a flow restrictor.

11. The cassette of claim 1, wherein the flow controller is an additional pumping system.

12. The cassette of claim 1, wherein the flow controller is a system having a plurality of tubing to restrict or increase an amount and rate of permeate flow.

* * * * *